US011186626B2

(12) United States Patent
Aman et al.

(10) Patent No.: US 11,186,626 B2
(45) Date of Patent: Nov. 30, 2021

(54) BROADLY NEUTRALIZING ANTIBODY TARGETING THE EBOLAVIRUS GLYCOPROTEIN INTERNAL FUSION LOOP

(71) Applicants: Integrated BioTherapeutics, Inc., Rockville, MD (US); THE UNIVERSITY OF MARYLAND, College Park, MD (US)

(72) Inventors: Mohammad Javad Aman, Rockville, MD (US); Katie A. Howell, North Bethesda, MD (US); Frederick Wayne Holtsberg, Taneytown, MD (US); Xuelian Zhao, Gaithersburg, MD (US); Yuxing Li, Boyds, MD (US)

(73) Assignees: INTEGRATED BIOTHERAPEUTICS, INC., Rockville, MD (US); UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

(21) Appl. No.: 16/340,996

(22) PCT Filed: Oct. 9, 2017

(86) PCT No.: PCT/US2017/055795
§ 371 (c)(1),
(2) Date: Apr. 10, 2019

(87) PCT Pub. No.: WO2018/071345
PCT Pub. Date: Apr. 19, 2018

(65) Prior Publication Data
US 2020/0040065 A1 Feb. 6, 2020

Related U.S. Application Data

(60) Provisional application No. 62/406,598, filed on Oct. 11, 2016.

(51) Int. Cl.
*C07K 16/10* (2006.01)
*A61K 39/42* (2006.01)
*A61K 47/68* (2017.01)
*A61P 31/14* (2006.01)
*A61K 39/00* (2006.01)

(52) U.S. Cl.
CPC .............. *C07K 16/10* (2013.01); *A61K 39/42* (2013.01); *A61K 47/6841* (2017.08); *A61K 2039/505* (2013.01); *A61P 31/14* (2018.01); *C07K 2317/31* (2013.01); *C07K 2317/33* (2013.01); *C07K 2317/515* (2013.01); *C07K 2317/565* (2013.01); *C07K 2317/76* (2013.01); *C12N 2760/14011* (2013.01); *C12N 2760/14022* (2013.01); *C12N 2760/14111* (2013.01); *C12N 2760/14122* (2013.01); *C12N 2760/14211* (2013.01); *C12N 2760/14222* (2013.01)

(58) Field of Classification Search
CPC .............. C07K 16/10; C07K 2317/515; C07K 2317/565; C07K 2317/76; A61K 39/42; C12N 2760/14222; C12N 2760/14122; C12N 2760/14111; C12N 2760/14211; C12N 2760/14011; C12N 2760/14022
See application file for complete search history.

(56) References Cited

U.S. PATENT DOCUMENTS

2009/0181015 A1  7/2009  Presta et al.

FOREIGN PATENT DOCUMENTS

| WO | 2016/068802 A1 | 5/2016 |
| WO | 2016069627 A1 | 5/2016 |
| WO | 2016/145385 A2 | 9/2016 |

OTHER PUBLICATIONS

Chen, C., et al., Sep. 1992, Generation and analysis of random point mutations in an antibody CDR2 sequence: Many mutated antibodies lose their ability to bind antigen, J. Exp. Med. 176:855-866.*
Li, Y., et al., 1996, The I binding specificity of human VH4-34 (VH4-21) encoded antibodies is determined by both VH framework region 1 and complementarity determining region 3, J. Mol. Biol. 256:577-589.*
Winkler, K., et al., 2000, Changing the antigen binding specificity by single point mutations of an anti-p24 (HIV-1) antibody, J. Immunol. 165:4505-4514.*
Kala et al., 2002, Phage displayed antibodies to heat stable alkaline phosphatase: Framework region as a determinant of specificity, J. Biochem. 132:535-541.*
Messaoudi, I., et al., Nov. 2015, Filovirus pathogenesis and immune evasion: insights from Ebolavirus and Marburg virus, Nat. Rev. Microbiol. 13:663-676.*
Saphire, E. O., and M. J. Aman, Sep. 2016, Feverish quest for Ebola immunotherapy: straight or cocktail? Trends Microbiol. 24(9):684-686.*
Extended European Search Report for EP Application No. 17859433.9 dated Jun. 9, 2020.

(Continued)

*Primary Examiner* — Jeffrey S Parkin
(74) *Attorney, Agent, or Firm* — Thompson Coburn LLP; William A. Holtz

(57) ABSTRACT

This disclosure provides a method for preventing, treating, or managing an ebolavirus infection in a subject, where the method includes administering to a subject in need thereof an effective amount of at least one pan-ebolavirus internal fusion loop antibody or antigen-binding fragment thereof, wherein the binding domain specifically binds to the epitope on two or more ebolavirus species or strains.

12 Claims, 8 Drawing Sheets

Figure 6:
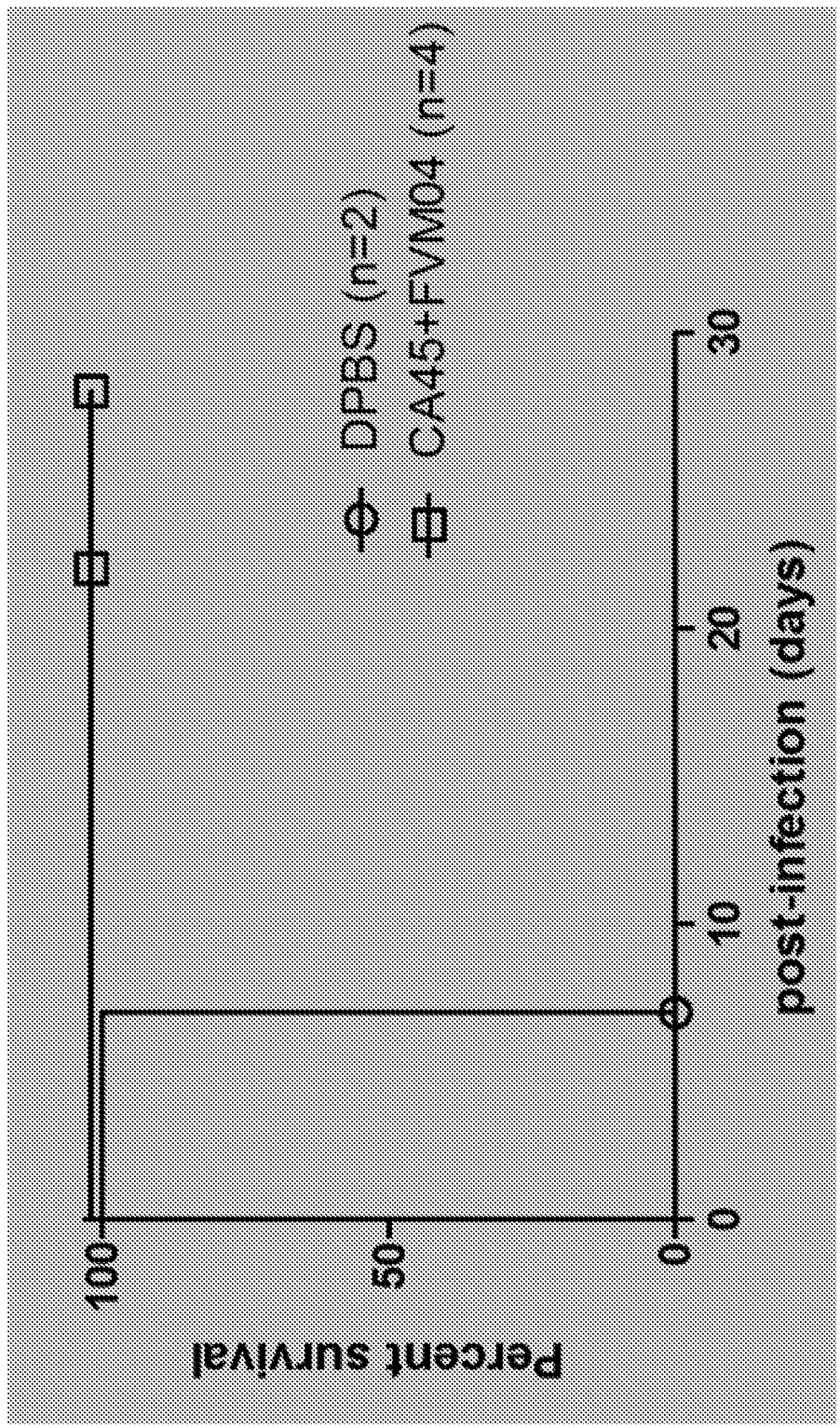

Specification includes a Sequence Listing.

(56) References Cited

OTHER PUBLICATIONS

Aman, "Chasing Ebola Through the Endosomal Labyrinth", mBio, 2016, pp. 1-3, vol. 7, No. 2.
Bornoldt et al., "Isolation of Potent Neutralizing Antibodies from a Surivorof the 2014 Ebola Virus Outbreak", Science, 2016, pp. 1078-1083, vol. 351, No. 6277.
Brannan et al., "Interferon a/b Receptor-Deficient Mice as a Model for Ebola Virus Disease", The Journal of Infectious Diseases, 2015, 13 pages, vol. 212.
Bray et al., "A Mouse Model for Evaluation of Prophylaxis and Therapy of Ebola Hemorrhagic Fever", The Journal of Infectious Diseases, 1999, 11 pages, vol. 179.
Brochet et al., "IMGT/V-QUEST: The Highly Customized and Integrated System for IG and TR Standardized V-J and V-D-J Sequence Analysis", Nucleic Acids Research, 2008, 5 pages, vol. 36.
Brummell et al., "Probing the Combining Site of an Anti-Carbohydrate Antibody by Saturation-Mutagenesis: Role of the Heavy-Chain CDR3 Residues", Biochemistry, 1993, pp. 1180-1187, vol. 32, No. 4.
Burks et al., "In Vitro Scanning Saturation Mutagenesis of an Antibody Binding Pocket", Proc. Natl. Acad. Sci. USA, 1997, pp. 412-417, vol. 94.
Chandran et al., "Endosomal Proteolysis of the Ebola Virus Glycoprotein is Necessary for Infection", Science, Jun. 10, 2005, pp. 1643-1645, vol. 308, Issue 5728.
Chothia et al., "Canonical Structures for the Hypervariable Regions of Immunoglobulins", Journal of Molecular biology, 1987, pp. 901-917, vol. 196.
Corti et al., "Protective Monotherapy Against Lethal Ebola Virus Infection by a Potently Neutralizing Antibody", Science, 2016, pp. 1339-1342, vol. 351, No. 6279.
Davidson et al., "A High-Throughput Shotgun Mutagenesis Approach to Mapping B-Cell Antibody Epitopes", Immunology, 2014, pp. 13-20, vol. 143.
Dube et al., "The Primed Ebolavirus Glycoprotein (19-Kilodalton GP 1,2): Sequence and Residues Critical for Host Cell Binding", Journal of Virology, Apr. 2009, pp. 2883-2891, vol. 83, No. 7.
Dye et al., "Postexposure Antibody Prophylaxis Protects Nonhuman Primates from Filovirus Disease", Proceedings of the National Academy of Science, Mar. 27, 2012, pp. 5034-5039, vol. 109, No. 13.
Feldmann et al., "Ebola Virus: From Discovery to Vaccine", Nature Reviews Immunology, Aug. 2003, pp. 677-685, vol. 3.
Feldmann et al., "Glycosylation and Oligomerization of the Spike Protein of Marburg Virus", Virology, 1991, pp. 353-356, vol. 182.
Feldmann et al., "Molecular Biology and Evolution of Filoviruses", Arch. Virol., 1993, pp. 81-100, vol. 7.
Feldmann et al., "Therapy and Prophylaxis of Ebola Virus Infections", Current Opinion in Investigational Drugs, 2005, pp. 823-830, vol. 6, No. 8.
Flyak et al., "Mechanism of Human Antibody-Mediated Neutralization of Marburg Virus", Cell, 2015, pp. 893-903, vol. 160.
Geisbert et al., "Differentiation of Filoviruses by Electron Microscopy", Virus Research, 1995, pp. 129-150, vol. 39.
Geisbert et al., "Prospects for Immunisation Against Marburg and Ebola Virus", Reviews in Medical Virology, Nov. 2010, pp. 344-357, vol. 20, No. 6.
Hashiguchi et al., "Structural Basis for Marburg Virus Neutralization by a Cross-Reactive Human Antibody", Cell, 2015, pp. 904-912, vol. 160.
Holtsberg et al., "Pan-Ebolavirus and Pan-Filovirus Mouse Monoclonal Antibodies: Protection Against Ebola and Sudan Viruses", Journal of Virology, 2016, pp. 266-278, vol. 90, No. 1.
Howell et al., "Antibody Treatment of Ebola and Sudan Virus Infection via a Uniquely Exposed Epitope Within the Glycoprotein Receptor-Binding Site", Cell Reports, 2016, pp. 1514-1526, vol. 15.
Kaletsky et al., "Proteolysis of the Ebola Virus Glycoproteins Enhances Virus Binding and Infectivity", Journal of Virology, Dec. 2007, pp. 13378-13384, vol. 81, No. 24.
Keck et al., "Macaque Monoclonal Antibodies Targeting Novel Conserved Epitopes Within Filovirus Glycoprotein", Journal of Virology, 2016, pp. 279-291, vol. 90, No. 1.
Kiley et al., "Physicochemical Properties of Marburg Virus: Evidence for Three Distinct Virus Strains and Their Relationship to Ebola Virus", J. Gen. Virol., 1988, pp. 1957-1967, vol. 69.
Kobayashi et al., "Tryptophan H33 Plays an Important Role in Pyrimidine (6-4) Pyrimidone Photoproduct Binding by a High-Affinity Antibody", Protein Engineering, 1999, pp. 879-884, vol. 12, No. 10.
Kozak et al., "Ferrets Infected with Bundibugyo Virus or Ebola Virus Recaitulate Important Aspects of Human Filovirus Disease", Journal of Virology, pp. 9209-9223, vol. 90, No. 20.
Kuhn et al., "Conserved Receptor-Binding Domains of Lake Victoria Marburgvirus and Zaire Ebolavirus Bind a Common Receptor", The Journal of Biological Chemistry, Jun. 9, 2006, pp. 15951-15958, vol. 281, No. 23.
Lee et al., "Neutralizing Ebolavirus: Structural Insights into the Envelope Glycoprotein and Antibodies Targeted Against it", Curr. Opin. Struct. Biol., 2009, pp. 408-417, vol. 19, No. 4.
Lee et al., "Structure of the Ebola Virus Glycoprotein Bound to an Antibody from a Human Survivor", Nature, Jul. 10, 2008, pp. 177-183, vol. 454.
Mabry et al., "Therapeutic Bispecific Antibodies: The Selection of Stable Single-Chain Fragments to Overcome Engineering Obstacles", IDrugs, 2010, pp. 543-549, vol. 13, No. 8.
Manicassamy et al., "Comprehensive Analysis of Ebola Virus GP1 in Viral Entry", Journal of Virology, 2005, pp. 4793-4805, vol. 79, No. 8.
Murin et al., "Structures of Protective Antibodies Reveal Sites of Vulnerability on Ebola Virus", PNAS, 2014, pp. 17182-17187, vol. 111, No. 48.
Olinger, Jr., et al., "Delayed Treatment of Ebola Virus Infection with Plant-Derived Monoclonal Antibodies Provides Protection in Rhesus Macaques", Proceedings of the National Academy of Sciences, Oct. 30, 2012, pp. 18030-18035, vol. 109, No. 44.
Qiu et al., "mAbs and Ad-Vectored IFN-a Therapy Rescue Ebola-Infected Nonhuman Primates When Administered After the Detection of Viremia and Symptoms", Science Translational Medicine, Oct. 16, 2013, 10 pages, vol. 5, Issue 207, 207ra143.
Qiu et al., "Monoclonal Antibodies Combined with Adenovirus-Vectored Interferon Significantly Extend the Treatment Window in Ebola Virus-Infected Guinea Pigs", Journal of Virology, Jul. 2013, pp. 7754-7757, vol. 87, No. 13.
Qiu et al., "Reversion of Advanced Ebola Virus Disease in Nonhuman Primates with ZMapp", Nature, 2014, 26 pages, vol. 514, No. 7520.
Roux et al., "Comparisons of the Ability of Human IgG3 Hinge Mutants, IgM, IgE, and IgA2, to Form Small Immune Complexes: A Role for Flexibility and Geometry", The Journal of Immunology, 1998, pp. 4083-4090, vol. 161.
Sanchez et al., "Biochemical Analysis of the Secreted and Virion Glycoproteins of Ebola Virus", Journal of Virology, 1998, pp. 6442-6447, vol. 72, No. 8.
Saphire et al., "Feverish Quest for Ebola Immunotherapy: Straight or Cocktail?", Trends in Microbiology, 2016, pp. 684-686, vol. 24, No. 9.
Saphire, "An Update on the Use of Antibodies Against the Filoviruses", Immunotherapy, 2013, pp. 1221-1233, vol. 5, No. 11.
Schornberg et al., "Role of Endosomal Cathepsins in Entry Mediated by the Ebola Virus Glycoprotein", Journal of Virology, Apr. 2006, pp. 4174-4178, vol. 80, No. 8.
Strohlein et al., "The Trifunctional Antibody Catumaxomab in Treatment of Malignant Ascites and Peritoneal Carcinomatosis", Future Oncology, 2010, pp. 1387-1394, vol. 6.
Sundling et al., "High-Resolution Definition of Vaccine-Elicited B Cell Responses Against the HIV Primary Receptor Binding Site", Science Translational Medicine, 9 pages, vol. 4, No. 142.

(56) References Cited

OTHER PUBLICATIONS

Warfield et al., "Induction of Humoral and CD8+ T Cell Responses Are Required for Protection Against Lethal Ebola Virus Infection", The Journal of Immunology, 2005, pp. 1184-1191, vol. 175.

* cited by examiner

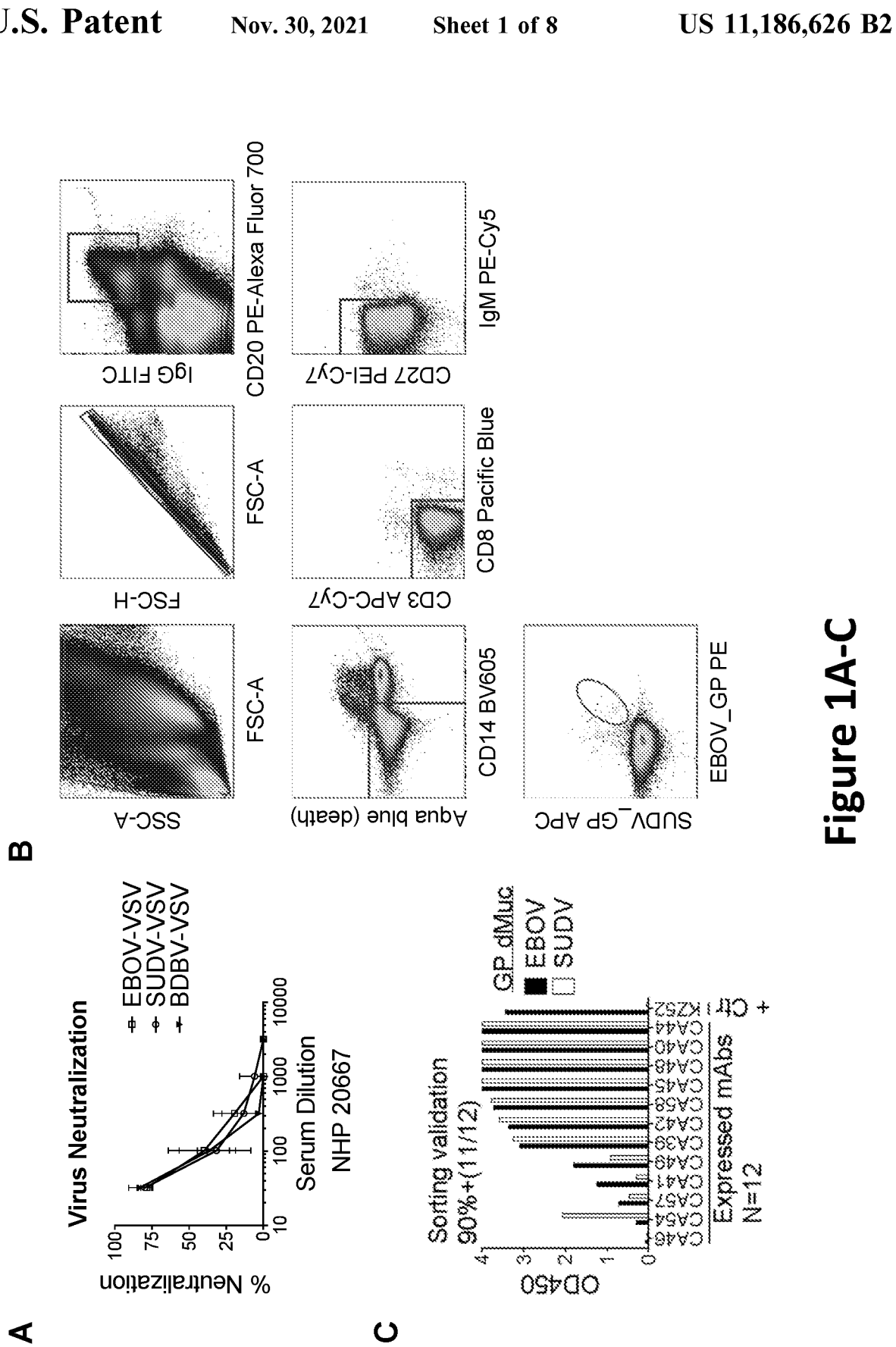
Figure 1A-C

A ELISA Binding

○ pH 7.5　⊠ pH 5.5　▼ pH 4.5

| | EC$_{50}$ (nM) | | |
|---|---|---|---|
| | pH 7.5 | pH 5.5 | pH 4.5 |
| EBOV GPΔTM | 1.41 ± 0.05 | 0.70 ± 0.03 | 0.65 ± 0.02 |
| SUDV GPΔTM | 2.35 ± 0.17 | 1.30 ± 0.10 | 0.71 ± 0.02 |
| BDBV GPΔTM | 0.34 ± 0.01 | 0.22 ± 0.01 | 0.21 ± 0.01 |
| RESTV GPΔTM | >10 | >10 | >10 |
| EBOV GP$_{CL}$ | 0.06 ± 0.00 | 0.05 ± 0.01 | 0.09 ± 0.02 |
| EBOV sGP | ND | ND | ND |

Figure 2A

Figure 2B

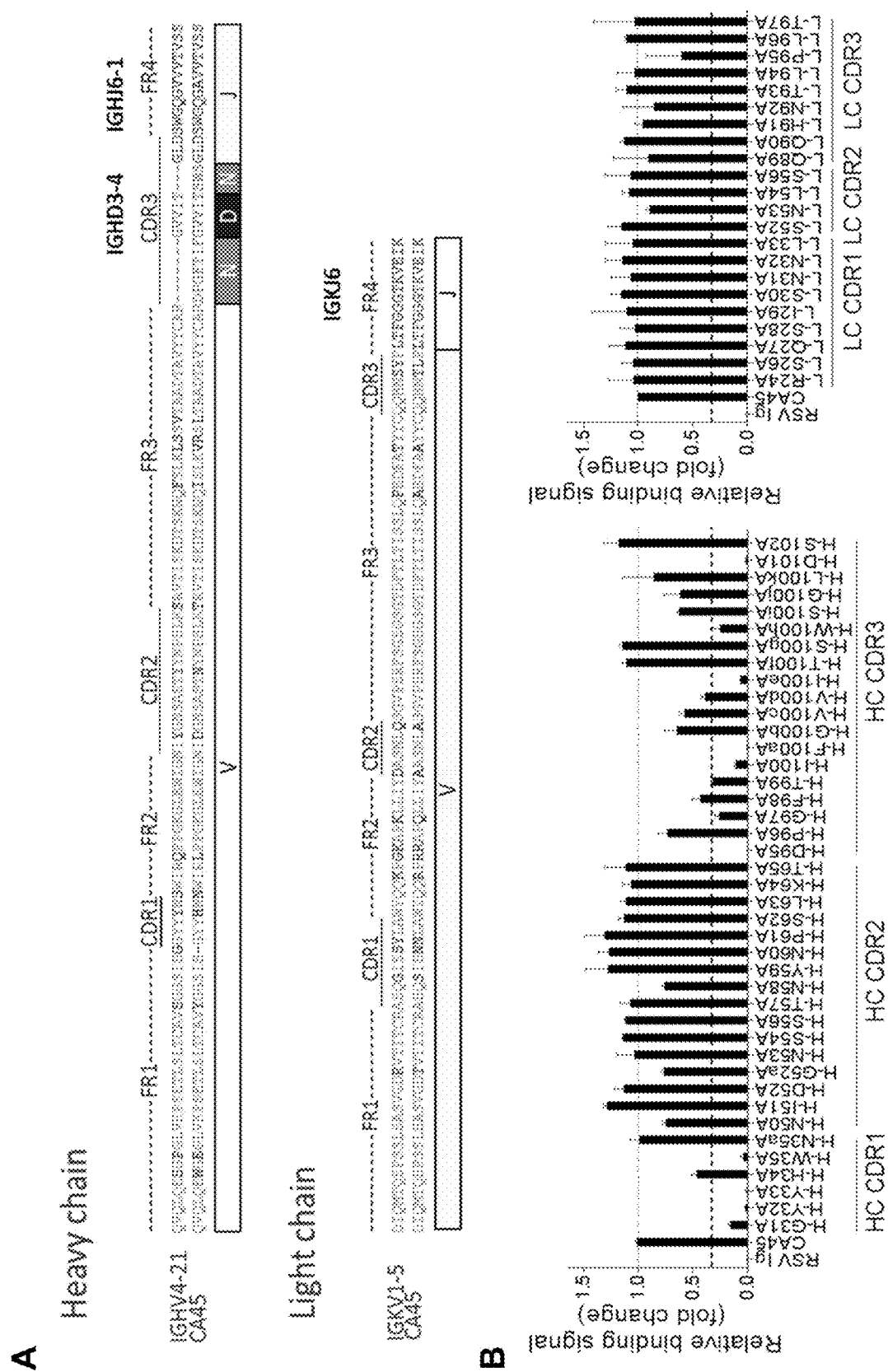
Figure 3A-B

C

| Mutations | Binding affinity relative to WT[a] EBOV GPΔMuc | SUDV GPΔMuc | BDBV GPΔTM |
|---|---|---|---|
| *CDRH1*[b] | | | |
| G31A | 0.16 | 0.59 | 0.54 |
| Y32A | 0.02 | 0.02 | 0.12 |
| Y33A | 0.01 | 0 | 0.01 |
| H34A | 0.46 | 0.5 | 0.68 |
| W35A | 0.04 | 0.06 | 0.07 |
| N35aA | 0.98 | 0.85 | 1.06 |
| *CDRH2* | | | |
| N50A | 0.74 | 1.02 | 1.07 |
| I51A | 1.28 | 1.16 | 1.22 |
| D52A | 1.12 | 1.34 | 1.18 |
| G52aA | 0.76 | 0.83 | 0.79 |
| N53A | 1.03 | 1.09 | 1 |
| S54A | 1.13 | 1.08 | 0.95 |
| S56A | 1.1 | 1.28 | 1.21 |
| T57A | 1.06 | 1.18 | 1.17 |
| N58A | 0.75 | 1.3 | 1.35 |
| Y59A | 1.27 | 1.26 | 1.23 |
| N60A | 1.26 | 1.21 | 1.28 |
| P61A | 1.3 | 1.2 | 1.22 |
| S62A | 1.12 | 1.16 | 1.1 |
| L63A | 1.1 | 1.15 | 1.2 |
| K64A | 1.05 | 1 | 1.14 |
| T65A | 1.1 | 1 | 1.07 |

| Mutations | Binding affinity relative to WT EBOV GPΔMuc | SUDV GPΔMuc | BDBV GPΔTM |
|---|---|---|---|
| *CDRH3* | | | |
| D95A | 0 | 0 | 0 |
| P96A | 0.73 | 0.91 | 0.74 |
| G97A | 0.28 | 0.79 | 0.93 |
| F98A | 0.43 | 0.52 | 0.81 |
| T99A | 0.32 | 0.35 | 0.71 |
| I100A | 0.11 | 0.31 | 0.38 |
| F100aA | 0.01 | 0 | 0.01 |
| G100bA | 0.64 | 0.74 | 0.8 |
| V100cA | 0.57 | 0.91 | 1.14 |
| V100dA | 0.39 | 0.5 | 0.57 |
| I100eA | 0.07 | 0.18 | 0.22 |
| T100fA | 1.1 | 0.97 | 0.84 |
| S100gA | 1.13 | 0.96 | 0.94 |
| W100hA | 0.25 | 0.3 | 0.33 |
| S100iA | 0.62 | 0.95 | 1.18 |
| G100jA | 0.61 | 0.66 | 0.56 |
| L100kA | 0.85 | 1.09 | 0.87 |
| D101A | 0.02 | 0.48 | 0 |
| S102A | 1.17 | 1.06 | 0.89 |

[a]WT affinity is defined as the value of 1
[b]CDRs are defined by Kabat system
Relative affinity < 0.33 (3-fold decrease) is highlighted

| Mutations | Binding affinity relative to WT EBOV GPΔMuc | SUDV GPΔMuc | BDBV GPΔTM |
|---|---|---|---|
| *CDRL1* | | | |
| R24A | 1.04 | 1.05 | 0.92 |
| S26A | 1.04 | 0.99 | 0.85 |
| Q27A | 1.11 | 1.05 | 1.06 |
| S28A | 1.03 | 1.13 | 0.99 |
| I29A | 1.1 | 1.17 | 0.97 |
| S30A | 1.15 | 1.13 | 1 |
| N31A | 1.07 | 1.14 | 1.04 |
| N32A | 1.14 | 1.15 | 1.04 |
| L33A | 1.05 | 1.1 | 1.08 |
| *CDRL2* | | | |
| S52A | 1.15 | 0.99 | 0.87 |
| N53A | 0.89 | 0.93 | 0.71 |
| L54A | 1.08 | 0.99 | 0.77 |
| S56A | 1.07 | 0.98 | 0.91 |
| *CDRL3* | | | |
| Q89A | 0.9 | 0.95 | 0.66 |
| Q90A | 1.13 | 1.03 | 0.93 |
| H91A | 0.96 | 1.04 | 0.8 |
| N92A | 0.85 | 1.04 | 0.79 |
| T93A | 1.1 | 1.16 | 0.95 |
| L94A | 1.03 | 1.18 | 0.95 |
| P95A | 0.6 | 1.03 | 0.68 |
| L96A | 1.11 | 1.03 | 0.85 |
| T97A | 1.03 | 1.18 | 0.87 |

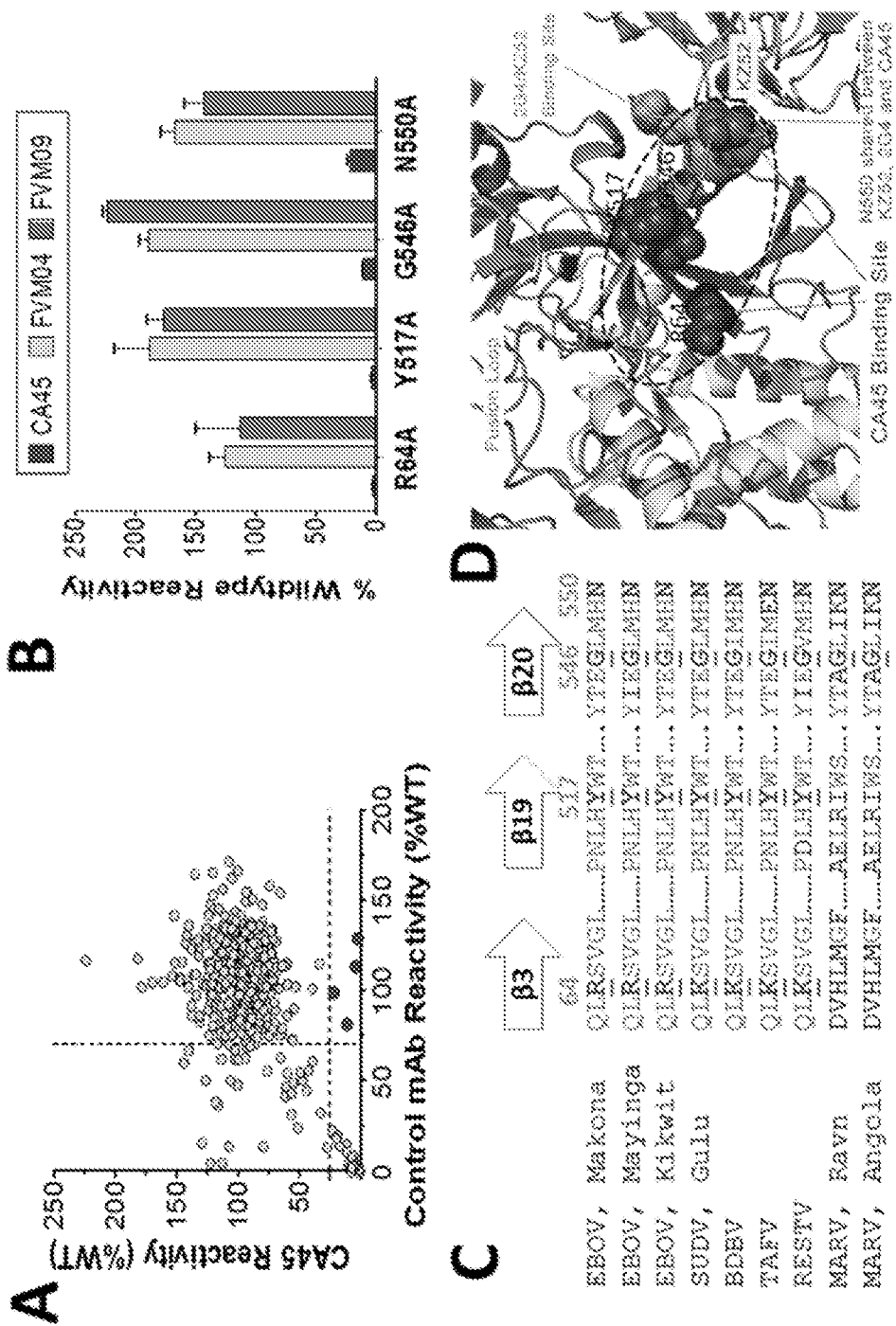
Figure 4A-D

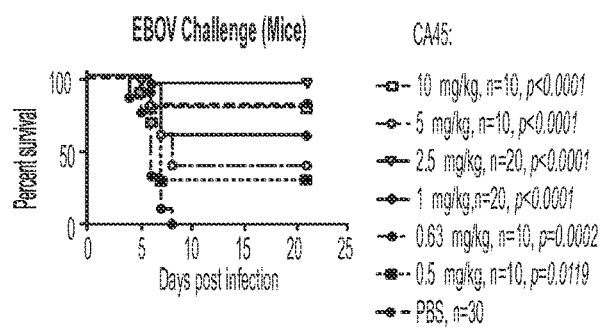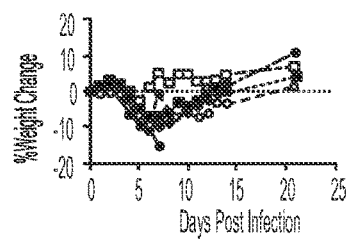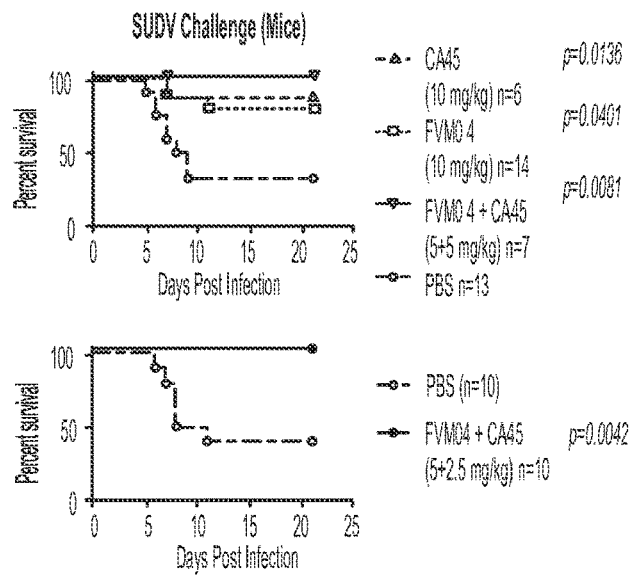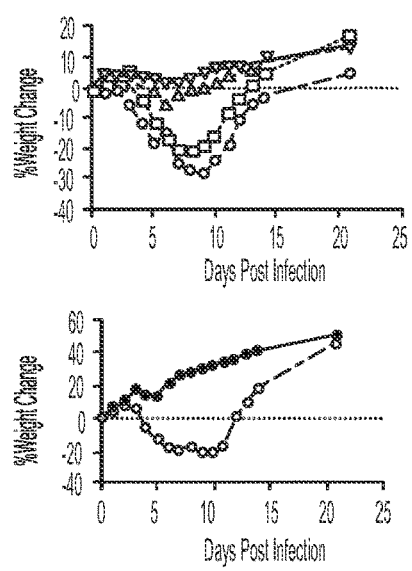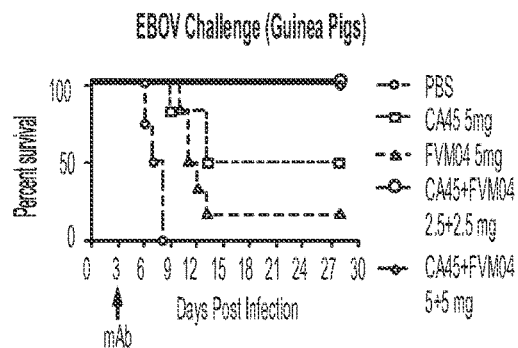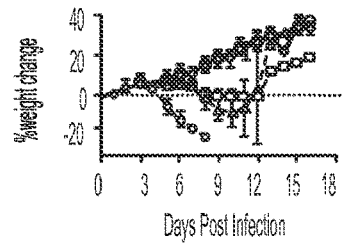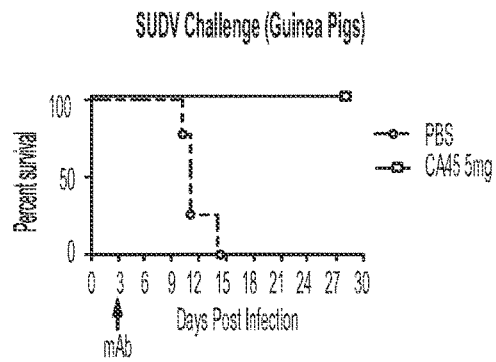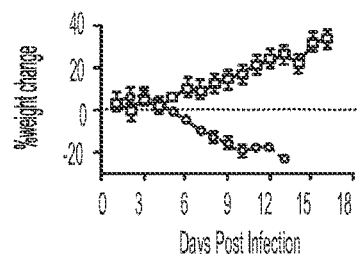
Figure 5A-D

SEQUENCE LISTING

<160> NUMBER OF SEQ ID NOS: 35

<210> SEQ ID NO 1
<211> LENGTH: 128
<212> TYPE: PRT
<213> ORGANISM: cynomolgus macaque

<400> SEQUENCE: 1

Gln Val Gln Leu Gln Glu Trp Gly Glu Gly Leu Val Lys Pro Ser Glu
1               5                   10                  15

Thr Leu Ser Leu Thr Cys Ala Val Tyr Gly Gly Ser Ile Ser Gly Tyr
            20                  25                  30

Tyr His Trp Asn Trp Ile Arg Leu Pro Pro Gly Lys Gly Leu Glu Trp
        35                  40                  45

Ile Gly Asn Ile Asp Asn Ser Ala Ser Thr Asn Tyr Asn Pro Ser Leu
    50                  55                  60

```
Lys Thr Arg Val Thr Ile Ser Lys Asp Thr Ser Lys Asn Gln Ile Ser
 65                  70                  75                  80

Leu Lys Val Arg Ser Leu Thr Ala Ala Asp Thr Ala Val Tyr Tyr Cys
                 85                  90                  95

Ala Arg Asp Pro Gly Phe Thr Ile Phe Gly Val Val Ile Thr Ser Trp
            100                 105                 110

Ser Gly Leu Asp Ser Trp Gly Gln Gly Ala Val Val Thr Val Ser Ser
            115                 120                 125

<210> SEQ ID NO 2
<211> LENGTH: 106
<212> TYPE: PRT
<213> ORGANISM: cynomolgus macaque

<400> SEQUENCE: 2

Asp Ile Gln Met Thr Gln Ser Pro Ser Ser Leu Ser Ala Ser Val Gly
 1               5                  10                  15

Asp Thr Val Thr Ile Thr Cys Arg Ala Ser Gln Ser Ile Ser Asn Asn
             20                  25                  30

Leu Ala Trp Tyr Gln Gln Arg Pro Arg Arg Ala Pro Gln Leu Leu Ile
         35                  40                  45

Tyr Ala Ala Ser Asn Leu Ala Ser Gly Val Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Phe Ala Ala Tyr Tyr Cys Gln Gln His Asn Thr Leu Pro Leu
                 85                  90                  95

Thr Phe Gly Gly Gly Thr Lys Val Glu Ile
            100                 105

<210> SEQ ID NO 3
<211> LENGTH: 6
<212> TYPE: PRT
<213> ORGANISM: cynomolgus macaque

<400> SEQUENCE: 3

Gly Tyr Tyr His Trp Asn
 1               5

<210> SEQ ID NO 4
<211> LENGTH: 17
<212> TYPE: PRT
<213> ORGANISM: cynomolgus macaque

<400> SEQUENCE: 4

Gly Asn Ile Asp Asn Ser Ala Ser Thr Asn Tyr Asn Pro Ser Leu Lys
 1               5                  10                  15

Thr

<210> SEQ ID NO 5
<211> LENGTH: 19
<212> TYPE: PRT
<213> ORGANISM: cynomolgus macaque

<400> SEQUENCE: 5

Asp Pro Gly Phe Thr Ile Phe Gly Val Val Ile Thr Ser Trp Ser Gly
 1               5                  10                  15

Leu Asp Ser
```

-continued

```
<210> SEQ ID NO 6
<211> LENGTH: 11
<212> TYPE: PRT
<213> ORGANISM: cynomolgus macaque

<400> SEQUENCE: 6

Arg Ala Ser Gln Ser Ile Ser Asn Asn Leu Ala
1               5                   10

<210> SEQ ID NO 7
<211> LENGTH: 6
<212> TYPE: PRT
<213> ORGANISM: cynomolgus macaque

<400> SEQUENCE: 7

Ala Ala Ser Asn Leu Ala
1               5

<210> SEQ ID NO 8
<211> LENGTH: 9
<212> TYPE: PRT
<213> ORGANISM: cynomolgus macaque

<400> SEQUENCE: 8

Gln Gln His Asn Thr Leu Pro Leu Thr
1               5

<210> SEQ ID NO 9
<211> LENGTH: 6
<212> TYPE: PRT
<213> ORGANISM: cynomolgus macaque
<220> FEATURE:
<221> NAME/KEY: misc_feature
<222> LOCATION: (1)..(6)
<223> OTHER INFORMATION: X is any amino acid

<400> SEQUENCE: 9

Gly Tyr Tyr Xaa Trp Xaa
1               5

<210> SEQ ID NO 10
<211> LENGTH: 19
<212> TYPE: PRT
<213> ORGANISM: cynomolgus macaque
<220> FEATURE:
<221> NAME/KEY: misc_feature
<222> LOCATION: (1)..(19)
<223> OTHER INFORMATION: X is any amino acid

<400> SEQUENCE: 10

Asp Xaa Gly Xaa Thr Ile Phe Xaa Xaa Xaa Ile Xaa Xaa Trp Xaa Xaa
1               5                   10                  15

Xaa Asp Xaa

<210> SEQ ID NO 11
<211> LENGTH: 676
<212> TYPE: PRT
<213> ORGANISM: Ebola virus

<400> SEQUENCE: 11

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
```

```
             35                  40                  45
Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
65                   70                  75                  80

Ser Val Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460
```

```
His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Arg Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 12
<211> LENGTH: 676
<212> TYPE: PRT
<213> ORGANISM: Ebola virus

<400> SEQUENCE: 12

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
```

```
            145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
            210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
            275                 280                 285
Ala Phe Trp Glu Thr Lys Lys Asn Leu Thr Arg Lys Ile Arg Ser Glu
290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
            355                 360                 365
Ala Thr Ile Ser Thr Ser Pro Gln Ser Leu Thr Thr Lys Pro Gly Pro
            370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
            435                 440                 445
Thr Thr Ser Pro Gln Asn His Ser Glu Thr Ala Gly Asn Asn Asn Thr
450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
            515                 520                 525
Leu Ala Trp Ile Pro Tyr Phe Gly Pro Ala Ala Glu Gly Ile Tyr Ile
            530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
```

```
Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 13
<211> LENGTH: 676
<212> TYPE: PRT
<213> ORGANISM: Ebola virus

<400> SEQUENCE: 13

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
```

-continued

```
                260                 265                 270
Leu Ile Trp Lys Val Asn Pro Glu Ile Asp Thr Thr Ile Gly Glu Trp
            275                 280                 285
Ala Phe Trp Glu Thr Lys Lys Asn Leu Thr Arg Lys Ile Arg Ser Glu
        290                 295                 300
Glu Leu Ser Phe Thr Ala Val Ser Asn Arg Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
        355                 360                 365
Ala Thr Ile Ser Thr Ser Pro Gln Pro Pro Thr Thr Lys Pro Gly Pro
        370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Pro Ala Thr Thr Ala Ala Gly Pro Leu Lys Ala
            420                 425                 430
Glu Asn Thr Asn Thr Ser Lys Gly Thr Asp Leu Leu Asp Pro Ala Thr
        435                 440                 445
Thr Thr Ser Pro Gln Asn His Ser Glu Thr Ala Gly Asn Asn Asn Thr
        450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Ala Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
        515                 520                 525
Leu Ala Trp Ile Pro Tyr Phe Gly Pro Ala Ala Glu Gly Ile Tyr Ile
        530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
Thr Glu Leu Arg Thr Phe Ser Ile Leu Asn Arg Lys Ala Ile Asp Phe
            580                 585                 590
Leu Leu Gln Arg Trp Gly Gly Thr Cys His Ile Leu Gly Pro Asp Cys
        595                 600                 605
Cys Ile Glu Pro His Asp Trp Thr Lys Asn Ile Thr Asp Lys Ile Asp
        610                 615                 620
Gln Ile Ile His Asp Phe Val Asp Lys Thr Leu Pro Asp Gln Gly Asp
625                 630                 635                 640
Asn Asp Asn Trp Trp Thr Gly Trp Arg Gln Trp Ile Pro Ala Gly Ile
                645                 650                 655
Gly Val Thr Gly Val Ile Ile Ala Val Ile Ala Leu Phe Cys Ile Cys
            660                 665                 670
Lys Phe Val Phe
        675
```

<210> SEQ ID NO 14
<211> LENGTH: 676
<212> TYPE: PRT
<213> ORGANISM: Ebola virus

<400> SEQUENCE: 14

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
        355                 360                 365

Glu Gly Arg Arg Val Gly Val Asn Thr Gln Glu Thr Ile Thr Glu Thr

```
        370                 375                 380
Ala Ala Thr Ile Ile Gly Thr Asn Gly Asn His Met Gln Ile Ser Thr
385                 390                 395                 400

Ile Gly Ile Arg Pro Ser Ser Gln Ile Pro Ser Ser Pro Thr
                405                 410                 415

Thr Ala Pro Ser Pro Glu Ala Gln Thr Pro Thr Thr His Thr Ser Gly
                420                 425                 430

Pro Ser Val Met Ala Thr Glu Glu Pro Thr Thr Pro Gly Ser Ser
            435                 440                 445

Pro Gly Pro Thr Thr Glu Ala Pro Thr Leu Thr Thr Pro Glu Asn Ile
            450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
                500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
            530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
                580                 585                 590

Leu Leu Arg Arg Trp Gly Gly Thr Cys Arg Ile Leu Gly Pro Asp Cys
            595                 600                 605

Cys Ile Glu Pro His Asp Trp Thr Lys Asn Ile Thr Asp Lys Ile Asn
            610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ala Ile Ile Ala Leu Leu Cys Val Cys
            660                 665                 670

Lys Leu Leu Cys
        675

<210> SEQ ID NO 15
<211> LENGTH: 676
<212> TYPE: PRT
<213> ORGANISM: Ebola virus

<400> SEQUENCE: 15

Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
                20                  25                  30

Ile Pro Leu Gly Val Val His Asn Asn Thr Leu Gln Val Ser Asp Ile
            35                  40                  45

Asp Lys Leu Val Cys Arg Asp Lys Leu Ser Ser Thr Ser Gln Leu Lys
        50                  55                  60
```

```
Ser Val Gly Leu Asn Leu Glu Gly Asn Gly Ala Thr Asp Val Pro
 65                  70                  75                  80

Thr Ala Thr Lys Arg Trp Gly Phe Arg Ala Gly Val Pro Lys Val
                 85                  90                  95

Val Asn Tyr Glu Ala Gly Glu Trp Ala Glu Asn Cys Tyr Asn Leu Asp
                100                 105                 110

Ile Lys Lys Ala Asp Gly Ser Glu Cys Leu Pro Glu Ala Pro Glu Gly
                115                 120                 125

Val Arg Gly Phe Pro Arg Cys Arg Tyr Val His Lys Val Ser Gly Thr
                130                 135                 140

Gly Pro Cys Pro Glu Gly Phe Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Lys Thr Lys Lys Asp
                180                 185                 190

Phe Phe Gln Ser Pro Pro Leu His Glu Pro Ala Asn Met Thr Thr Asp
                195                 200                 205

Pro Ser Ser Tyr Tyr His Thr Val Thr Leu Asn Tyr Val Ala Asp Asn
210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
                260                 265                 270

Leu Ile Trp Lys Val Asn Pro Thr Val Asp Thr Gly Val Gly Glu Trp
                275                 280                 285

Ala Phe Trp Glu Asn Lys Lys Asn Phe Thr Lys Thr Leu Ser Ser Glu
                290                 295                 300

Glu Leu Ser Val Ile Leu Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Lys Asp Pro Ala Ser Val Val Gln
                340                 345                 350

Val Arg Asp Leu Gln Arg Glu Asn Thr Val Pro Thr Ser Pro Leu Asn
                355                 360                 365

Thr Val Pro Thr Thr Leu Ile Pro Asp Thr Met Glu Glu Gln Thr Thr
                370                 375                 380

Ser His Tyr Glu Leu Pro Asn Ile Ser Gly Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Gln Asp Gly Glu Arg Thr Ser Ser His Thr
                420                 425                 430

Thr Pro Ser Pro Arg Pro Val Pro Thr Ser Thr Ile His Pro Thr Thr
                435                 440                 445

Arg Glu Thr Gln Ile Pro Thr Thr Met Ile Thr Ser His Asp Thr Asp
                450                 455                 460

Ser Asn Arg Pro Asn Pro Ile Asp Ile Ser Glu Ser Thr Glu Pro Gly
465                 470                 475                 480

Leu Leu Thr Asn Thr Ile Arg Gly Val Ala Asn Leu Leu Thr Gly Ser
```

-continued

```
                485                 490                 495
Arg Arg Thr Arg Arg Glu Ile Thr Leu Arg Thr Gln Ala Lys Cys Asn
                500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
        530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
        610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 16
<211> LENGTH: 676
<212> TYPE: PRT
<213> ORGANISM: Ebola virus

<400> SEQUENCE: 16

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
        35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175
```

-continued

```
Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
            195                 200                 205

Pro Ser Ser Tyr Tyr His Thr Thr Ile Asn Tyr Val Val Asp Asn
            210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
            245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
            275                 280                 285

Ala Phe Trp Glu Asn Lys Lys Asn Phe Thr Lys Thr Leu Ser Ser Glu
            290                 295                 300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Ala
            325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Thr Val Thr Gly
            355                 360                 365

Val Pro Thr Thr Thr Pro Ser Pro Phe Pro Ile Asn Ala Arg Asn Thr
370                 375                 380

Asp His Thr Lys Ser Phe Ile Gly Leu Glu Gly Pro Gln Glu Asp His
385                 390                 395                 400

Ser Thr Thr Gln Pro Ala Lys Thr Thr Ser Gln Pro Thr Asn Ser Thr
            405                 410                 415

Glu Ser Thr Thr Leu Asn Pro Thr Ser Glu Pro Ser Ser Arg Gly Thr
            420                 425                 430

Gly Pro Ser Ser Pro Thr Val Pro Asn Thr Thr Glu Ser His Ala Glu
            435                 440                 445

Leu Gly Lys Thr Thr Pro Thr Thr Leu Pro Glu Gln His Thr Ala Ala
            450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Leu Thr Gly Ser
            485                 490                 495

Arg Arg Lys Arg Arg Asp Val Thr Pro Asn Thr Gln Pro Lys Cys Asn
            500                 505                 510

Pro Asn Leu His Tyr Trp Thr Ala Leu Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
```

```
                           595                 600                 605

Cys Ile Glu Pro Gln Asp Trp Thr Lys Asn Ile Thr Asp Lys Ile Asp
            610                 615                 620

Gln Ile Ile His Asp Phe Val Asp Asn Asn Leu Pro Asn Gln Asn Asp
        625                 630                 635                 640

Gly Ser Asn Trp Trp Thr Gly Trp Lys Gln Trp Val Pro Ala Gly Ile
                            645                 650                 655

Gly Ile Thr Gly Val Ile Ile Ala Ile Ile Ala Leu Leu Cys Ile Cys
                        660                 665                 670

Lys Phe Met Leu
                        675

<210> SEQ ID NO 17
<211> LENGTH: 677
<212> TYPE: PRT
<213> ORGANISM: Ebola virus

<400> SEQUENCE: 17

Met Gly Ser Gly Tyr Gln Leu Leu Gln Leu Pro Arg Glu Arg Phe Arg
1               5                   10                  15

Lys Thr Ser Phe Leu Val Trp Ala Ile Ile Leu Phe Gln Arg Ala Ile
                20                  25                  30

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
    50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Pro Pro Pro Asp
        115                 120                 125

Gly Val Arg Gly Phe Pro Arg Cys Arg Tyr Val His Lys Val Gln Gly
    130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Ala Glu Gly Val Ile Ala Phe Leu Ile Leu Ser Glu Pro Arg Lys
            180                 185                 190

His Phe Trp Lys Ala Thr Pro Ala His Glu Pro Val Asn Thr Thr Asp
        195                 200                 205

Asp Ser Thr Ser Tyr Tyr Ile Thr Leu Thr Leu Ser Tyr Glu Met Ser
    210                 215                 220

Asn Phe Gly Gly Glu Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255

Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asn Val Gly Glu
        275                 280                 285
```

```
Trp Ala Phe Trp Glu Thr Lys Lys Asn Phe Ser Lys Gln Leu Gln Gly
    290                 295                 300
Glu Asn Leu His Phe Gln Ile Leu Ser Thr His Thr Asn Asn Ser Ser
305                 310                 315                 320
Asp Gln Ser Pro Ala Gly Thr Val Gln Gly Lys Ile Ser Tyr His Pro
                325                 330                 335
Pro Thr Asn Asn Ser Glu Leu Val Pro Thr Asp Ser Pro Pro Val Val
            340                 345                 350
Ser Val Leu Thr Ala Gly Arg Thr Glu Glu Met Ser Thr Gln Gly Leu
        355                 360                 365
Thr Asn Gly Glu Thr Ile Thr Gly Phe Thr Ala Asn Pro Met Thr Thr
370                 375                 380
Thr Ile Ala Leu Ser Pro Thr Met Thr Ser Lys Val Asp Asn Asn Val
385                 390                 395                 400
Pro Ser Glu Gln Pro Asn Asn Thr Thr Ser Ile Glu Asp Ser Pro Pro
                405                 410                 415
Ser Ala Ser Asn Glu Thr Ile Asp His Ser Glu Met Asn Ser Ile Gln
            420                 425                 430
Gly Ser Asn Asn Ser Thr Gln Ser Pro Gln Thr Lys Thr Lys Pro Ala
        435                 440                 445
Pro Thr Ala Ser Leu Met Thr Leu Gly Pro Gln Glu Thr Ala Asn Ser
450                 455                 460
Ser Lys Pro Gly Thr Ser Pro Gly Ser Ala Ala Glu Pro Ser Gln Pro
465                 470                 475                 480
Gly Leu Thr Ile Asn Thr Val Ser Lys Val Ala Asp Ser Leu Ser Pro
                485                 490                 495
Thr Arg Lys Gln Lys Arg Ser Val Arg Gln Asn Thr Ala Asn Glu Cys
            500                 505                 510
Asn Pro Asp Leu His Tyr Trp Thr Ala Val Asp Glu Gly Ala Ala Val
        515                 520                 525
Gly Leu Ala Trp Ile Pro Tyr Phe Gly Pro Ala Ala Glu Gly Ile Tyr
530                 535                 540
Ile Glu Gly Val Met His Asn Gln Asn Gly Leu Ile Cys Gly Leu Arg
545                 550                 555                 560
Gln Leu Ala Asn Glu Thr Thr Gln Ala Leu Gln Leu Phe Leu Arg Ala
                565                 570                 575
Thr Thr Glu Leu Arg Thr Tyr Ser Leu Leu Asn Arg Lys Ala Ile Asp
            580                 585                 590
Phe Leu Leu Gln Arg Trp Gly Gly Thr Cys Arg Ile Leu Gly Pro Ser
        595                 600                 605
Cys Cys Ile Glu Pro His Asp Trp Thr Lys Asn Ile Thr Asp Glu Ile
610                 615                 620
Asn Gln Ile Lys His Asp Phe Ile Asp Asn Pro Leu Pro Asp His Gly
625                 630                 635                 640
Asp Asp Leu Asn Leu Trp Thr Gly Trp Arg Gln Trp Ile Pro Ala Gly
                645                 650                 655
Ile Gly Ile Ile Gly Val Ile Ile Ala Ile Thr Ala Leu Leu Cys Ile
            660                 665                 670
Cys Lys Ile Leu Cys
        675

<210> SEQ ID NO 18
<211> LENGTH: 681
<212> TYPE: PRT
```

-continued

<213> ORGANISM: Marburg virus

<400> SEQUENCE: 18

```
Met Lys Thr Ile Tyr Phe Leu Ile Ser Leu Ile Leu Ile Gln Ser Ile
1               5                   10                  15

Lys Thr Leu Pro Val Leu Glu Ile Ala Ser Asn Ser Gln Pro Gln Asp
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Leu Asp Pro Pro Ser Asn
            100                 105                 110

Ile Arg Asp Tyr Pro Lys Cys Lys Thr Val His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Val Ala Ser Thr Thr Met Tyr Arg Gly Lys Val Phe
145                 150                 155                 160

Thr Glu Gly Asn Ile Ala Ala Met Ile Val Asn Lys Thr Val His Arg
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Glu Thr Gln Arg Asn Asp
        195                 200                 205

Thr Gly Cys Phe Gly Ile Leu Gln Glu Tyr Asn Ser Thr Asn Asn Gln
    210                 215                 220

Thr Cys Pro Pro Ser Leu Lys Pro Pro Ser Leu Pro Thr Val Thr Pro
225                 230                 235                 240

Ser Ile His Ser Thr Asn Thr Gln Ile Asn Thr Ala Lys Ser Gly Thr
                245                 250                 255

Met Asn Pro Ser Ser Asp Asp Glu Asp Leu Met Ile Ser Gly Ser Gly
            260                 265                 270

Ser Gly Glu Gln Gly Pro His Thr Thr Leu Asn Val Val Thr Glu Gln
        275                 280                 285

Lys Gln Ser Ser Thr Ile Leu Ser Thr Pro Ser Leu His Pro Ser Thr
    290                 295                 300

Ser Gln His Glu Gln Asn Ser Thr Asn Pro Ser Arg His Ala Val Thr
305                 310                 315                 320

Glu His Asn Gly Thr Asp Pro Thr Thr Gln Pro Ala Thr Leu Leu Asn
                325                 330                 335

Asn Thr Asn Thr Thr Pro Thr Tyr Asn Thr Leu Lys Tyr Asn Leu Ser
            340                 345                 350

Thr Pro Ser Pro Pro Thr Arg Asn Ile Thr Asn Asn Asp Thr Gln Arg
        355                 360                 365

Glu Leu Ala Glu Ser Glu Gln Thr Asn Ala Gln Leu Asn Thr Thr Leu
    370                 375                 380

Asp Pro Thr Glu Asn Pro Thr Thr Gly Gln Asp Thr Asn Ser Thr Thr
385                 390                 395                 400
```

```
Asn Ile Ile Met Thr Thr Ser Asp Ile Thr Ser Lys His Pro Thr Asn
                405                 410                 415
Ser Ser Pro Asp Ser Ser Pro Thr Thr Arg Pro Pro Ile Tyr Phe Arg
            420                 425                 430
Lys Lys Arg Ser Ile Phe Trp Lys Glu Gly Asp Ile Phe Pro Phe Leu
        435                 440                 445
Asp Gly Leu Ile Asn Thr Glu Ile Asp Phe Asp Pro Ile Pro Asn Thr
    450                 455                 460
Glu Thr Ile Phe Asp Glu Ser Pro Ser Phe Asn Thr Ser Thr Asn Glu
465                 470                 475                 480
Glu Gln His Thr Pro Pro Asn Ile Ser Leu Thr Phe Ser Tyr Phe Pro
                485                 490                 495
Asp Lys Asn Gly Asp Thr Ala Tyr Ser Gly Glu Asn Glu Asn Asp Cys
            500                 505                 510
Asp Ala Glu Leu Arg Ile Trp Ser Val Gln Glu Asp Asp Leu Ala Ala
        515                 520                 525
Gly Leu Ser Trp Ile Pro Phe Phe Gly Pro Gly Ile Glu Gly Leu Tyr
    530                 535                 540
Thr Ala Gly Leu Ile Lys Asn Gln Asn Asn Leu Val Cys Arg Leu Arg
545                 550                 555                 560
Arg Leu Ala Asn Gln Thr Ala Lys Ser Leu Glu Leu Leu Leu Arg Val
                565                 570                 575
Thr Thr Glu Glu Arg Thr Phe Ser Leu Ile Asn Arg His Ala Ile Asp
            580                 585                 590
Phe Leu Leu Thr Arg Trp Gly Gly Thr Cys Lys Val Leu Gly Pro Asp
        595                 600                 605
Cys Cys Ile Gly Ile Glu Asp Leu Ser Lys Asn Ile Ser Glu Gln Ile
    610                 615                 620
Asp Lys Ile Arg Lys Asp Glu Gln Lys Glu Glu Thr Gly Trp Gly Leu
625                 630                 635                 640
Gly Gly Lys Trp Trp Thr Ser Asp Trp Gly Val Leu Thr Asn Leu Gly
                645                 650                 655
Ile Leu Leu Leu Leu Ser Ile Ala Val Leu Ile Ala Leu Ser Cys Ile
            660                 665                 670
Cys Arg Ile Phe Thr Lys Tyr Ile Gly
        675                 680

<210> SEQ ID NO 19
<211> LENGTH: 681
<212> TYPE: PRT
<213> ORGANISM: Marburg virus

<400> SEQUENCE: 19

Met Lys Thr Thr Cys Leu Leu Ile Ser Leu Ile Leu Ile Gln Gly Val
1               5                   10                  15
Lys Thr Leu Pro Ile Leu Glu Ile Ala Ser Asn Ile Gln Pro Gln Asn
                20                  25                  30
Val Asp Ser Val Cys Ser Gly Thr Leu Gln Lys Thr Glu Asp Val His
            35                  40                  45
Leu Met Gly Phe Thr Leu Ser Gly Gln Lys Val Ala Asp Ser Pro Leu
    50                  55                  60
Glu Ala Ser Lys Arg Trp Ala Phe Arg Ala Gly Val Pro Pro Lys Asn
65                  70                  75                  80
Val Glu Tyr Thr Glu Gly Glu Glu Ala Lys Thr Cys Tyr Asn Ile Ser
                85                  90                  95
```

```
Val Thr Asp Pro Ser Gly Lys Ser Leu Leu Asp Pro Thr Asn
        100                 105                 110
Ile Arg Asp Tyr Pro Lys Cys Lys Thr Ile His His Ile Gln Gly Gln
        115                 120                 125
Asn Pro His Ala Gln Gly Ile Ala Leu His Leu Trp Gly Ala Phe Phe
    130                 135                 140
Leu Tyr Asp Arg Ile Ala Ser Thr Thr Met Tyr Arg Gly Lys Val Phe
145                 150                 155                 160
Thr Glu Gly Asn Ile Ala Ala Met Ile Val Asn Lys Thr Val His Lys
                165                 170                 175
Met Ile Phe Ser Arg Gln Gly Gln Gly Tyr Arg His Met Asn Leu Thr
            180                 185                 190
Ser Thr Asn Lys Tyr Trp Thr Ser Ser Asn Gly Thr Gln Thr Asn Asp
        195                 200                 205
Thr Gly Cys Phe Gly Thr Leu Gln Glu Tyr Asn Ser Thr Lys Asn Gln
    210                 215                 220
Thr Cys Ala Pro Ser Lys Lys Pro Leu Pro Leu Pro Thr Ala His Pro
225                 230                 235                 240
Glu Val Lys Leu Thr Ser Thr Ser Thr Asp Ala Thr Lys Leu Asn Thr
                245                 250                 255
Thr Asp Pro Asn Ser Asp Asp Glu Asp Leu Thr Thr Ser Gly Ser Gly
            260                 265                 270
Ser Gly Glu Gln Glu Pro Tyr Thr Thr Ser Asp Ala Ala Thr Lys Gln
        275                 280                 285
Gly Leu Ser Ser Thr Met Pro Pro Thr Pro Ser Pro Gln Pro Ser Thr
    290                 295                 300
Pro Gln Gln Gly Gly Asn Asn Thr Asn His Ser Gln Gly Val Val Thr
305                 310                 315                 320
Glu Pro Gly Lys Thr Asn Thr Thr Ala Gln Pro Ser Met Pro Pro His
                325                 330                 335
Asn Thr Thr Thr Ile Ser Thr Asn Asn Thr Ser Lys His Asn Leu Ser
            340                 345                 350
Thr Pro Ser Val Pro Ile Gln Asn Ala Thr Asn Tyr Asn Thr Gln Ser
        355                 360                 365
Thr Ala Pro Glu Asn Glu Gln Thr Ser Ala Pro Ser Lys Thr Thr Leu
    370                 375                 380
Leu Pro Thr Glu Asn Pro Thr Thr Ala Lys Ser Thr Asn Ser Thr Lys
385                 390                 395                 400
Ser Pro Thr Thr Thr Val Pro Asn Thr Thr Asn Lys Tyr Ser Thr Ser
                405                 410                 415
Pro Ser Pro Thr Pro Asp Ser Thr Ala Gln His Leu Val Tyr Phe Arg
            420                 425                 430
Arg Lys Arg Asn Ile Leu Trp Arg Glu Gly Asp Met Phe Pro Phe Leu
        435                 440                 445
Asp Gly Leu Ile Asn Ala Pro Ile Asp Phe Asp Pro Val Pro Asn Thr
    450                 455                 460
Lys Thr Ile Phe Asp Glu Ser Ser Ser Gly Ala Ser Ala Glu Glu
465                 470                 475                 480
Asp Gln His Ala Ser Pro Asn Ile Ser Leu Thr Leu Ser Tyr Phe Pro
                485                 490                 495
Lys Val Asn Glu Asn Thr Ala His Ser Gly Glu Asn Glu Asn Asp Cys
            500                 505                 510
```

```
Asp Ala Glu Leu Arg Ile Trp Ser Val Gln Glu Asp Leu Ala Ala
            515                 520                 525

Gly Leu Ser Trp Ile Pro Phe Phe Gly Pro Gly Ile Glu Gly Leu Tyr
        530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
            565                 570                 575

Thr Thr Glu Glu Arg Thr Phe Ser Leu Ile Asn Arg His Ala Ile Asp
            580                 585                 590

Phe Leu Leu Ala Arg Trp Gly Gly Thr Cys Lys Val Leu Gly Pro Asp
        595                 600                 605

Cys Cys Ile Gly Ile Glu Asp Leu Ser Arg Asn Ile Ser Glu Gln Ile
        610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
            645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680

<210> SEQ ID NO 20
<211> LENGTH: 118
<212> TYPE: PRT
<213> ORGANISM: rhesus macaque

<400> SEQUENCE: 20

Glu Val Gln Leu Val Gln Ser Gly Gly Gly Leu Val Gln Pro Gly Gly
1               5                   10                  15

Ser Met Arg Leu Ser Cys Glu Ala Ser Gly Leu Ser Leu Ser Asp Tyr
            20                  25                  30

Phe Met His Trp Val Arg Gln Ala Gln Gly Lys Gly Leu Glu Trp Ile
        35                  40                  45

Gly Leu Ile Gln Thr Lys Ala Phe Thr Tyr Lys Thr Glu Tyr Pro Ala
    50                  55                  60

Ala Val Lys Gly Arg Phe Thr Ile Ser Arg Asp Asp Ser Lys Asn Thr
65                  70                  75                  80

Leu Tyr Leu Gln Met Ser Ser Leu Lys Pro Glu Asp Thr Ala Leu Tyr
                85                  90                  95

Tyr Cys Ile Ala Val Thr Pro Asp Phe Tyr Tyr Trp Gly Gln Gly Val
            100                 105                 110

Leu Val Thr Val Ser Ser
        115

<210> SEQ ID NO 21
<211> LENGTH: 110
<212> TYPE: PRT
<213> ORGANISM: rhesus macaque

<400> SEQUENCE: 21

Asp Val Val Met Thr Gln Ser Pro Ser Phe Leu Ser Ala Ser Val Gly
1               5                   10                  15

Asp Arg Val Thr Ile Thr Cys Arg Ala Ser Gln Asp Ile Thr Ile Asn
            20                  25                  30
```

```
Leu Asn Trp Phe Gln His Lys Pro Gly Lys Ala Pro Lys Arg Leu Ile
             35                  40                  45

Tyr Val Ala Ser Arg Leu Glu Arg Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Pro Gly Thr Lys Leu Asp Ile Lys Arg Thr Val
            100                 105                 110

<210> SEQ ID NO 22
<211> LENGTH: 10
<212> TYPE: PRT
<213> ORGANISM: rhesus macaque

<400> SEQUENCE: 22

Gly Leu Ser Leu Ser Asp Tyr Phe Met His
 1               5                  10

<210> SEQ ID NO 23
<211> LENGTH: 10
<212> TYPE: PRT
<213> ORGANISM: rhesus macaque

<400> SEQUENCE: 23

Ile Gln Thr Lys Ala Phe Thr Tyr Lys Thr
 1               5                  10

<210> SEQ ID NO 24
<211> LENGTH: 9
<212> TYPE: PRT
<213> ORGANISM: rhesus macaque

<400> SEQUENCE: 24

Ile Ala Val Thr Pro Asp Phe Tyr Tyr
 1               5

<210> SEQ ID NO 25
<211> LENGTH: 6
<212> TYPE: PRT
<213> ORGANISM: rhesus macaque

<400> SEQUENCE: 25

Gln Asp Ile Thr Ile Asn
 1               5

<210> SEQ ID NO 26
<211> LENGTH: 3
<212> TYPE: PRT
<213> ORGANISM: rhesus macaque

<400> SEQUENCE: 26

Val Ala Ser
 1

<210> SEQ ID NO 27
<211> LENGTH: 9
<212> TYPE: PRT
<213> ORGANISM: rhesus macaque

<400> SEQUENCE: 27

Gln Gln Tyr Asn Asn Tyr Pro Leu Thr
```

<210> SEQ ID NO 28
<211> LENGTH: 119
<212> TYPE: PRT
<213> ORGANISM: cynomolgus macaque

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Tyr Tyr Trp Ser Trp Ile Arg Gln Pro Pro Gly Lys Gly Leu Glu
        35                  40                  45

Trp Ile Gly Asn Ile Tyr Asn Ser Ala Ser Thr Tyr Tyr Asn Pro Ser
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Ile Thr Gly Leu Asp Ser Trp Gly Gln Gly
            100                 105                 110

Val Val Val Thr Val Ser Ser
        115

<210> SEQ ID NO 29
<211> LENGTH: 106
<212> TYPE: PRT
<213> ORGANISM: cynomolgus macaque

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Ser Tyr Pro Leu
                85                  90                  95

Thr Phe Gly Gly Gly Thr Lys Val Glu Ile
            100                 105

<210> SEQ ID NO 30
<211> LENGTH: 7
<212> TYPE: PRT
<213> ORGANISM: Ebola virus

<400> SEQUENCE: 30

Gln Leu Arg Ser Val Gly Leu
1               5

<210> SEQ ID NO 31
<211> LENGTH: 7
<212> TYPE: PRT
<213> ORGANISM: Ebola virus

```
<400> SEQUENCE: 31

Pro Asn Leu His Tyr Trp Thr
1               5

<210> SEQ ID NO 32
<211> LENGTH: 8
<212> TYPE: PRT
<213> ORGANISM: Ebola virus

<400> SEQUENCE: 32

Tyr Thr Glu Gly Leu Met His Asn
1               5

<210> SEQ ID NO 33
<211> LENGTH: 7
<212> TYPE: PRT
<213> ORGANISM: Marburg virus

<400> SEQUENCE: 33

Asp Val His Leu Met Gly Phe
1               5

<210> SEQ ID NO 34
<211> LENGTH: 7
<212> TYPE: PRT
<213> ORGANISM: Marburg virus

<400> SEQUENCE: 34

Ala Glu Leu Arg Ile Trp Ser
1               5

<210> SEQ ID NO 35
<211> LENGTH: 8
<212> TYPE: PRT
<213> ORGANISM: Marburg virus

<400> SEQUENCE: 35

Tyr Thr Ala Gly Leu Ile Lys Asn
1               5
```

BROADLY NEUTRALIZING ANTIBODY TARGETING THE EBOLAVIRUS GLYCOPROTEIN INTERNAL FUSION LOOP

CROSS-REFERENCE AND RELATED APPLICATIONS

This application is a 35 U.S.C. § 371 National Phase Application of International Application No. PCT/US2017/055795, filed Oct. 9, 2017, which claims the benefit of U.S. Provisional Application Ser. No. 62/406,598 filed on Oct. 11, 2016, both of which are incorporated herein by reference in their entireties.

STATEMENT REGARDING FEDERALLY-SPONSORED RESEARCH AND DEVELOPMENT

This invention was made with government support under Grant No. AI098178 awarded by the National Institutes of Health. This invention was made with government support under Contract No. HDTRA-13-C-0015 awarded by the Defense Threat Reduction Agency (DTRA). The government has certain rights in the invention.

SEQUENCE LISTING STATEMENT

A sequence listing containing the file named IBT_170243-SEQ-LIST-ST25.txt which is 65536 bytes (measured in MS-Windows®) and created on Oct. 9, 2017, comprises 35 sequences, is provided herewith via the USPTO's EFS system, and is incorporated herein by reference in its entirety.

BACKGROUND

Filoviruses, e.g., of the genera ebolavirus and marburgvirus, cause severe hemorrhagic fevers in humans, with mortality rates reaching 88% (Feldmann, et al., 2003, *Nat Rev Immunol.* 3 (8):677-685) as well as epizootic diseases in nonhuman primates (NHP) and probably other mammals. Due to the high fatality rates and the potential for aerosol transmission, filoviruses have been classified as Category A NIAID Priority Pathogens. There are currently no commercially available vaccines or therapeutics against filoviruses. The main filovirus species causing outbreaks in humans are from the genus of ebolaviruses, e.g., Ebola virus (EBOV), Sudan ebolavirus, (SUDV), Reston ebolavirus (RESTV), Bundibugyo ebolavirus (BDBV), Tai Forest ebolavirus (TAFV). Filoviruses are enveloped, single-stranded, negative sense RNA filamentous viruses and encode seven proteins, of which the spike glycoprotein (GP) is considered the main protective antigen. The EBOV GP is proteolytically cleaved by furin protease into two subunits linked by a disulfide linkage: GP1 (~140 kDa) and GP2 (~38 kDa) (Manicassamy, et al., 2005, *J Virol*, 79 (8):4793-4805). Three GP1-GP2 units form the trimeric GP envelope spike (~550 kDa) on the viral surface (Feldmann, et al., 1993, *Arch Virol Suppl*, 7:81-100; Feldmann, et al., 1991, *Virology*, 182 (1):353-356; Geisbert and Jahrling, 1995, *Virus Res*, 39 (2-3):129-150; Kiley, et al., 1988a, *J Gen Virol*, 69 (Pt 8):1957-1967). GP1 mediates cellular attachment (Kiley, et al., 1988b, *J Gen Virol*, 69 (Pt 8):1957-1967; Kuhn, et al., 2006, *J Biol Chem*, 281 (23):15951-15958), and contains a mucin-like domain (MLD) which is heavily glycosylated and variable and has little or no predicted secondary structure (Sanchez, et al., 1998, *J Virol*, 72 (8):6442-6447). Other filoviruses include Marburg virus (MARV), and Lloviu virus (LLOV).

It is well established that the filovirus GPs represent the primary protective antigens (Feldmann, et al., 2003, *Nat Rev Immunol*, 3 (8):677-685; Feldmann, et al., 2005, *Curr Opin Investig Drugs*, 6 (8):823-830; Geisbert, et al., 2010, *Rev Med Virol*, 20(6):344-57). GP consists of a receptor binding GP1 subunit connected with the GP2 fusion domain via a disulfide link. A specific region of the MARV and EBOV GP1 has been previously identified consisting of ~150 amino acids (Kuhn, et al., 2006, *J Biol Chem*, 281 (23):15951-15958) that binds filovirus receptor-positive cells, but not receptor-negative cells, more efficiently than GP1, and competes with the entry of the respective viruses (Kuhn, et al., 2006, *J Biol Chem*, 281 (23):15951-15958). This region of GP is referred to here as receptor binding region (RBR) and is part of a larger domain that excludes the highly variable, glycosylated, and bulky mucin-like domain (MLD). The RBR shows the highest level of homology between Filovirus glycoproteins (Kuhn, et al., 2006, *J Biol Chem*, 281 (23):15951-15958). Therefore, the RBR represents a potential target for pan-filovirus antibodies.

The crystal structure of a trimeric, pre-fusion conformation of EBOV GP (lacking MLD) in complex with an EBOV-specific neutralizing antibody, KZ52, was solved at 3.4 Å (Lee, et al., 2008, *Nature*, 454 (7201):177-182). In this structure, three GP1 subunits assemble to form a chalice, cradled in a pedestal of the GP2 fusion subunits, while the MLD restricts access to the conserved RBR, sequestered in the GP chalice bowl. Ebola and Marburg GPs are cleaved by cathepsin proteases as an essential step in entry reducing GP1 to an ~18 kDa product associated with GP2 (trimeric cleaved GP, $GP_{CL}$) (Chandran, et al., 2005, *Science*, 308 (5728):1643-1645; Kaletsky, et al., 2007, *J Virol*, 81 (24):13378-13384; Schornberg, et al., 2006, *J Virol*, 80 (8):4174-4178). The structures suggest that the most likely site of cathepsin cleavage is the flexible β13-β14 loop of GP1 and illustrate how cleavage there would release the heavily glycosylated regions from GP, leaving just the core of GP1, encircled by GP2, with the RBR now well exposed. Cathepsin cleavage enhances attachment, presumably as a result of better exposing the RBR for interaction with cell surface factors trafficked with the virus into the endosome (Dube, et al., 2009, *J Virol*, 83:2883-2891). On the surface of the authentic virus, the MLD probably dominates host-interaction surfaces of filovirus GP, and indeed, antibodies against the MLD have been frequently identified. The seclusion of the receptor binding region (RBR) in the full length GP and its exposure during entry in the endosome suggest that targeting of neutralizing antibodies that recognize RBR to the endosomes may be useful in achieving effective neutralization of the filoviruses. The monoclonal antibody FVM04 is a prototypic inhibitors of receptor binding and consistent with the conserved nature of the RBR, FVM04 cross neutralizes multiple ebolaviruses and protects against Ebola virus and Sudan virus infections in animal models (Howell, et al., 2016, *Cell Rep*, 15(7):1514-26).

$GP_{CL}$-NPC1 interaction positions the internal fusion domain (IFL) of GP to interact with the endosomal membrane and trigger viral membrane fusion. While $GP_{CL}$-NPC1 interaction is required for membrane fusion, it is not sufficient. (Aman, 2016, *MBio*, 7(2):e00346-16). This process of fusion triggering involves major conformational rearrangement that are only partially understood likely dependent of acid and protease dependent processes that still remain to be defined in details. The trigger unwinds the GP2 helical structure from around the GP1 positioning IFL next to the endosomal membrane and allowing it to penetrate the endosomal membrane. As a result the pre-hairpin intermediate pulls together the viral and endosomal membrane, leading to hemifusion followed by formation of a fusion pore and post-fusion six helix bundle structure (Lee and Saphire, 2009, *Curr Opin Struct Biol* 19:408-17; Aman, 2016, *MBio*, 7(2):e00346-16). The virus then delivers its content through this pore into the host cytoplasm. The IFL consists of a two-strand beta sheet and a connecting loop that wrap arounds GP1. The Monoclonal antibodies KZ52 bind a species specific epitope at the base of the IFL (Lee, et al., 2008, *Nature*, 454 (7201):177-182). While binding to this epitope by KZ52-like antibodies leads to potent inhibition of viral fusion, the epitope is highly specific to EBOV (Zaire) and KZ52 does not cross react with other ebolaviruses (Saphire, 2013, *Immunotherapy*, 5(11):1221-33). Thus development of therapeutic antibodies that inhibit the fusion of multiple ebolaviruses is highly desirable. Such antibodies would likely bind to the stem (the beta sheets β19 and β20 (Lee, et al., 2008, *Nature*, 454 (7201):177-182)) or the tip of the IFL. We have previously reported that FVM02, a mAb that binds to the tip of the fusion loop but does not contact GP1, is unable to neutralize ebolaviruses. In contrast every neutralizing antibody that binds to the base of the GP trimer and neutralizes the virus contacts both GP1 and GP2, effectively bracing the two subunits (Saphire and Aman, 2016, *Trends Microbiol.*, 24(9):684-686). This bracing effect most likely mechanically interferes with the structural rearrangements required for productive fusion (Saphire and Aman, 2016, *Trends Microbiol.*, 24(9):684-686). The IFL closely interacts with GP1 particularly with the residues in the β3 strand (such as R64) as well as the N-terminal portion of the cathepsin cleavage loop (The loop consists of residues A189-Y214) suggesting that antibodies that contact both GP1 and GP2 residues in this region can brace the GP1 and GP2 and inhibit fusion.

Role of Antibodies in Protection against filovirus hemorrhagic fever: While both T and B cell responses are reported to play a role in protective immune responses to filoviruses (Warfield, et al., 2005, *J Immunol*, 175 (2):1184-1191), a series of recent reports indicate that antibody alone can provide significant protection. Dye et al. showed that purified convalescent IgG from macaques can protect NHS against challenge with MARV and EBOV when administered as late as 48 h post exposure (Dye, et al., 2012, *Pros Natl Acad Sic USA*, 109(13):5034-9). Linger et al. reported significant protection from EBOV challenge in NHPs treated with a cocktail of three monoclonal antibodies (mAbs) to GP administered 24 h and 48 h post exposure (Olinger, et al., 2012, *Proc Natl Acad Sci USA*, 109 (44):18030-18035). Similar results were also reported in two other studies (Qiu, et al., 2013, *Sci Transl Med*, 5 (207):207ra143; Qiu, et al., 2013, *J Virol*, 87 (13):7754-7757). A recent study shows that a combination of three monoclonal antibodies called ZMAPP™ can protect monkeys when administered five days after exposure to EBOV, at a time when the disease is fully manifest and the viremia is at its peak (Qiu, et al., 2014, *Nature*, 514:47-53). Collectively these data demonstrate the ability of the humoral response to control filovirus infection. While ZMAPP™ is strictly specific for EBOV, recent reports show that development off antibodies with broad neutralizing and protective property is feasible (WO2016/069627 and Keck, et al., 2015, *J Virol*, 90:279-291; WO2015/200522A2 and Holtsberg, et al., 2015, *J Virol*, 90:266-278; Howell et al. 2016, *Cell Reports*, 15, 1514-1526).

SUMMARY

The disclosure provides an isolated antibody or antigen-binding fragment thereof that includes a binding domain that specifically binds to an orthologous epitope in the internal fusion loop of an ebolavirus glycoprotein. In certain aspects the binding domain specifically binds to the epitope on two or more ebolavirus species or strains. In certain aspects, the antibody or fragment thereof binds to the same epitope as a reference antibody that includes a heavy chain variable region with the amino acid sequence SEQ ID NO: 1, and a light chain variable region with the amino acid sequence SEQ ID NO: 2. In certain aspects, the binding domain can specifically bind to the orthologous epitope as expressed in at least two of Ebola virus (EBOV), Sudan virus (SUDV), Bundibugyo virus (BDBV), or Reston virus (RESTV), e.g., the orthologous epitope as expressed in a mature EBOV glycoprotein derived from the precursor amino acid sequence SEQ ID NO: 11, SEQ ID NO: 12, or SEQ ID NO: 13; as expressed in a mature SUDV glycoprotein derived from the precursor amino acid sequence SEQ ID NO: 14; as expressed in a mature BDBV glycoprotein derived from the precursor amino acid sequence SEQ ID NO: 15; or as expressed in a mature RESTV glycoprotein derived from the precursor amino acid sequence SEQ ID NO: 17. In certain aspects, the orthologous epitope includes amino acids corresponding to R64 of SEQ ID NO: 11 or K64 of SEQ ID NO: 14, Y517 of SEQ ID NO: 11, G546 of SEQ ID NO: 11, and N 550 of SEQ ID NO: 11.

In certain aspects, the binding domain can include a heavy chain variable region (VH) and a light chain variable region (VL); where the VH includes heavy chain complementarity determining regions CDRH1, CDRH2, and CDRH3, where CDRH1 includes SEQ ID NO: 3 or SEQ ID NO: 3 with one or two single amino acid substitutions, where the substitutions are at positions X1 and/or X2 of G-Y-Y-X1-W-X2 (SEQ ID NO: 9); where CDRH2 includes SEQ ID NO: 4, or SEQ ID NO: 4 with one, two, or three single amino acid substitutions; and where CDRH3 includes SEQ ID NO: 5 or SEQ ID NO: 5 with one, two, or three single amino acid substitutions, where the substitutions are at positions X1, X2, X3, X4, X5, X6, X7, X8, X9, X10, X11, and/or X12 of D-X1-G-X2-T-I-F-X3-X4-X5-I-X6-X7-W-X8-X9-X10-D-X12 (SEQ ID NO: 10); and where the VL includes light chain complementarity determining regions CDRL1, CDRL2, and CDRL3, where CDRL1 includes SEQ ID NO: 6, or SEQ ID NO: 6 with one, two, or three single amino acid substitutions; where CDRL2 includes SEQ ID NO: 7, or SEQ ID NO: 7 with one, two, or three single amino acid substitutions; and where CDRL3 includes SEQ ID NO: 8, or SEQ ID NO: 8 with one, two, or three single amino acid substitutions. In certain aspects, the amino acid at position X1 of SEQ ID NO: 9 is substituted with alanine, the amino acid at position X2 of SEQ ID NO: 9 is substituted with alanine, or the amino acids at positions X1 and X2 of SEQ ID NO: 9 are substituted with alanine. In certain aspects, any one amino acid at position X1, X2, X3, X4, X5, X6, X7, X8, X9, X10, X11, or X12 of SEQ ID NO: 10 is substituted with alanine, any two amino acids at positions X1, X2, X3, X4, X5, X6, X7, X8, X9, X10, X11, or X12 of SEQ ID NO: 10 are substituted with alanine, or any three amino acids at positions X1, X2, X3, X4, X5, X6, X7, X8, X9, X10, X11, or X12 of SEQ ID NO: 10 are substituted with alanine. In certain aspects, CDRH1 comprises SEQ ID NO: 3 and CDRH3 comprises SEQ ID NO: 5.

In certain aspects, the VH can include an amino acid sequence at least 80%, 85%, 90%, 95%, or 100% identical to SEQ ID NO: 1, and the VL can include an amino acid sequence at least 80%, 85%, 90%, 95%, or 100% identical to SEQ ID NO: 2.

The disclosure further provides polynucleotides, vectors, and host cells that encode or express the provided antibody. Also provided are methods of making the antibody, and diagnostic and therapeutic methods that utilize the antibody.

BRIEF DESCRIPTION OF THE DRAWINGS/FIGURES

FIG. 1A-C: Isolation of broadly neutralizing mAb CA45 from GP-immunized cynomolgus macaque. (A) The neutralizing capacity of the serum of GP-immunized cynomolgus macaque, 20667, at week 12 time point (28 days post the $3^{rd}$ immunization) was assessed against pseudotype virus of three virus strains of ebolaviruses, EBOV, SDUV and BDBV, respectively. The macaque serum displayed moderate cross-neutralization capacity, with $ID_{50}$ values approximate to 80-100, the reciprocal dilution of serum at which 50% of virus entry is inhibited in neutralization assay. (B) Single B cell sorting of cross-reactive GP-specific monoclonal antibodies by flow cytometry. PBMCs obtained from macaque 20667 at the week 12 time point were incubated with cell markers and sorting probes consisting of EBOV and SUDV GPΔmuc. Cross-reactive memory B cells with the phenotype of $CD20^+IgG^+$Aqua blue$^-CD14^-CD3^-CD8^-CD27^+IgM^-$) as well as dual reactivity with GPs (EBOV $GP\Delta muc^{hi}$ SDUV $GP\Delta muc^{hi}$) were sorted into 96-well microtiter plates for Ig heavy- and light-chain gene amplification. (C) Initial validation of GP cross-reactive mAb FACS sorting and cloning precision by ELISA binding assay. IgG1 molecules from 12 selected sorted cells were expressed with paired heavy- and light-chain genes and tested for binding specificity for EBOV and SUDV GPΔmuc. >90% cloned mAb IgGs were positive for both GP ligands.

Figure 2B:
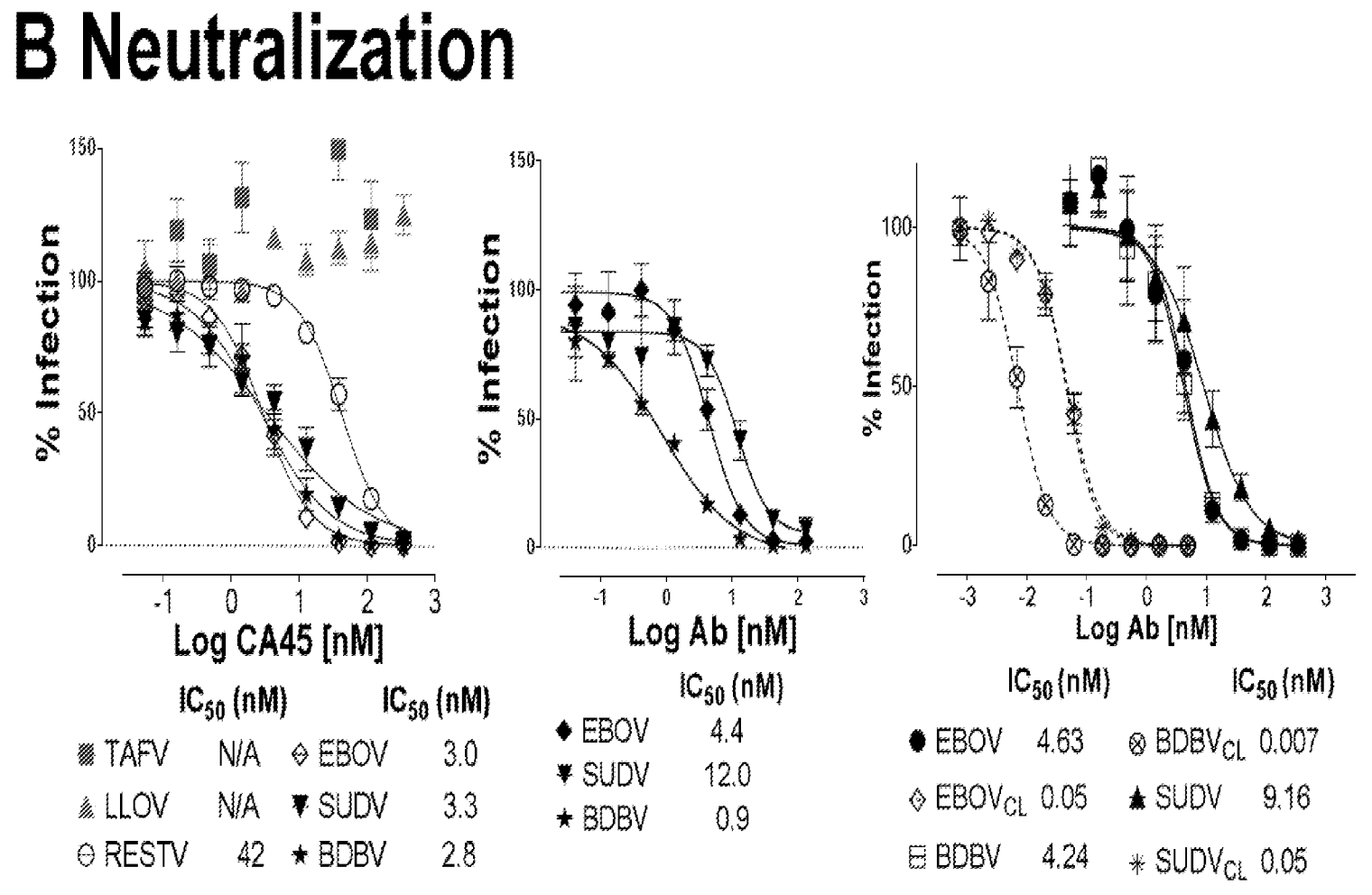

FIG. 2A-B: Binding characteristics and neutralizing activity of CA45. (A) Reactivity of CA45 to glycoprotein ectodomains (GPΔTM) of EBOV, SUDV, BDBV, and RESTV, as well as EBOV $GP_{CL}$ and sGP determined by ELISA at neutral and acidic pH. $EC_{50}$ values (nM) for each antigen and each condition are shown. (B) Neutralization of rVSV pseudotyped with ebolavirus glycoproteins by CA45. Left panel: Neutralization dose response of CA45 using replication competent rVSV-GFP-TAFV, -LLOV, -RESTV, -EBOV, -SUDV, and -BDBV in Vero cells. Middle panel: Neutralization dose response of CA45 using replication incompetent rVSV-Luc-EBOV, -SUDV, and -BDBV in Vero cells. Right panel: CA45 mediated neutralization of thermolysin cleaved rVSV-GFP-GP (subscript CL) in comparison to non-cleaved rVSV-GFP-GP.

FIG. 3A-C: CA45 heavy- and light-chain gene sequence and critical residues for GP recognition. (A) Sequence analysis of CA45 heavy and light chains (SEQ ID NO: 1 and SEQ ID NO: 2, respectively) with alignment to respective cynomolgus macaque Ig germline gene (V-(D)-J) segments as well as the N region that serves as the junction between VH-DH and DH-JH segments (IGHV4-21, SEQ ID NO: 28; IGKV1-5, SEQ ID NO: 29). (B) Alanine scanning mutants of CA45 heavy (HC, left) and light chain (LC, right) CDR loops were assessed for binding affinity for EBOV GPΔmuc relative to the wildtype (WT) IgG molecule. Mutated residues with relative binding signal <0.33 (with relative affinity decreases more than 3-folds) were considered to be critical for EBOV GP binding. (C) Summary of CA45 heavy—(left) and light-chain (right) CDR loop critical residues for EBOV, SUDV and BDBV binding. Mutated residues with relative binding signal <0.33 were considered as critical residues for GP binding and highlighted in blue.

FIG. 4A-D: CA45 Epitope mapping. (A) The EBOV GP shotgun alanine substitution library was tested for reactivity with CA45. Clones with <25% binding relative to that of wild-type EBOV GP yet >65% reactivity for a control mAb were initially identified to be critical for CA45 binding. (B) Mutation of four individual residues reduced CA45 binding (red bars) but did not reduce the binding of FVM04 and FVM09 (gray bars). Bars represent the mean and range of at least two replicate data points. (C) Homology between filovirus GP sequences within the regions encompassing the critical residues for CA45 binding. The full-length GP precursor sequences are presented herein as SEQ ID Nos 11-19. Conserved residues are shown in blue and CA45 critical residues in red. The corresponding beta strands in EBOV GP structure are shown on the top. 33 QLRSVGL (SEQ ID NO: 30), 1319 PNLHYWT (SEQ ID NO: 31), 1320 YTEGLMHN (SEQ ID NO: 32), β3 DVHLMGF (SEQ ID NO: 33), β19 AELRIWS (SEQ ID NO: 34), J320 YTAGLIKN (SEQ ID NO: 35). (D) Position of GP residues critical for CA45 in the structure of trimeric EBOV GP.

FIG. 5A-D: Efficacy in mouse and guinea pig models. (A) Groups of 10 or 20 BALB/c mice were infected with 100 pfu of MA-EBOV and treated with IP a single injection of indicated doses of CA45 or PBS as control at 2 dpi and monitored for 21 days. P values for each treatment group compared to the PBS was determined by Log-rank (Mantel-Cox) test. (B) A129 mice were infected with 1000 pfu of wild type SUDV and treated at 1 dpi with a single IP injection of FVM04, CA45, or combination of the two mAbs at indicated doses. Control group received PBS. Animals were monitored for 21 days. (C) Hartley guinea pigs were infected with 1000 $LD_{50}$ of GPA-EBOV and treated at 3 dpi by IP injection of FVM04, CA45, or the cocktail (n=6 each) or PBS (n=4). Animals were monitored for 28 days. P values: CA45 vs. PBS 0.0018, FVM04 vs. PBS 0.0018, cocktails vs. PBS <0.0001, CA45 vs. cocktails 0.0079, FVM04 vs. cocktails <0.0001. (D) Guinea pigs were challenged with GPA-SUDV and treated with 5 mg CA45 (n=6) or PBS (n=4) at 3 dpi and monitored for 28 days. P<0.0001.

FIG. 6: Four ferrets were infected with Bundibugyo virus (BDBV) and treated with a combination of 20 mg of FVM04 and 20 mg CA45 on days 3 and 6 post-infection. Two animals were infected and received PBS on days 3 and 6 post infection as controls.

DETAILED DESCRIPTION

The term "a" or "an" entity refers to one or more of that entity; for example, "a polypeptide subunit" is understood to represent one or more polypeptide subunits. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or could be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or could be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Variant polypeptides can also be referred to herein as "polypeptide analogs." As used herein a "derivative" refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1187 (1993); Kobayashi et al., *Protein Eng.* 12(10):879-884 (1999); and Burks et al., *Proc. Natl. Acad. Sci. USA* 94: 412-417 (1997)).

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. As described further herein, a binding molecule can comprise one or more "binding domains." As used herein, a "binding domain" or "antigen binding domain" is a two- or three-dimensional structure, e.g., a polypeptide structure that can specifically bind a given antigenic determinant, or epitope. One example of a binding domain is the region formed by the heavy and light chain variable regions of an antibody or fragment thereof. A non-limiting example of a binding molecule is an antibody or fragment thereof that comprises a binding domain that specifically binds an antigenic determinant or epitope. Another example of a binding molecule is a bispecific antibody comprising a first binding domain binding to a first epitope, and a second binding domain binding to a second epitope.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody, e.g., an antibody combine to form the variable region that defines a three dimensional antigen binding site. This quaternary antibody structure forms the antigen-binding site present at the end of each arm of the Y. More specifically, the antigen-binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196: 901-917 (1987), which are incorporated herein by reference, where the definitions include overlapping or subsets of amino acids when compared against each other. Nevertheless, application of either definition to refer to a CDR of an antibody or variants thereof is intended to be within the scope of the term as defined and used herein. The appropriate amino acids that encompass the CDRs as defined by each of the above-cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

|  | Kabat | Chothia |
|---|---|---|
| CDRH1 | 31-35 | 26-32 |
| CDRH2 | 50-65 | 52-58 |
| CDRH3 | 95-102 | 95-102 |
| CDRL1 | 24-34 | 26-32 |
| CDRL2 | 50-56 | 50-52 |
| CDRL3 | 89-97 | 91-96 |

*Numbering of CDR definitions in Table 1 is according to the numbering conventions set forth by Kabat et al. (see below).

Immunoglobulin variable domains can also be analyzed using the IMGT information system (on the world wide web at imgt.cines.fr) (IMGT®/V-Quest) to identify variable region segments, including CDRs. See, e.g., Brochet, X. et al., Nucl. Acids Res. 36:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is meant that a binding molecule, e.g., an antibody or fragment, variant, or derivative thereof binds to an epitope via its antigen binding domain, and that the binding entails some complementarity between the antigen binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

This disclosure provides a pan-ebolavirus GP antibody or a fragment thereof that specifically binds to the internal fusion loop of the GP2 subunit. A "pan-ebolavirus internal fusion loop antibody" as the term is used herein can include any portion of an antibody binding domain, e.g., a single CDR, three CDRs, six CDRs, a VH, a VL, or any combination thereof derived from, e.g., a human (e.g., a convalescent patient), a mouse, and/or a non-human primate (NHP), e.g., a rhesus macaque (*Macaca mulatta*), or a cynomolgus macaque (*Macaca fascicularis*).

A pan-ebolavirus internal fusion loop antibody or fragment, variant, or derivative thereof disclosed herein can be said to bind a target antigen, e.g., an ebolavirus glycoprotein disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. A pan-ebolavirus internal fusion loop antibody as disclosed herein can be said to bind a target antigen, e.g., an ebolavirus glycoprotein, with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A pan-ebolavirus internal fusion loop antibody or antigen-binding fragment, variant, or derivative disclosed herein can be said to bind a target antigen, e.g., an ebolavirus glycoprotein, with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. A pan-ebolavirus internal fusion loop antibody as disclosed herein can be said to bind a target antigen, e.g., an ebolavirus glycoprotein, with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A pan-ebolavirus internal fusion loop antibody or fragment, variant, or derivative thereof can be said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A pan-ebolavirus internal fusion loop antibody can be said to competitively inhibit binding of the reference antibody or antigen-binding fragment to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Antibodies or antigen-binding fragments, variants or derivatives thereof as disclosed herein can also be described or specified in terms of their cross-reactivity. As used herein, the term "cross-reactivity" refers to the ability of a pan-ebolavirus internal fusion loop antibody or fragment, variant, or derivative thereof, specific for one antigen, to react with a second antigen; a measure of relatedness between two different antigenic substances. Thus, an antibody is cross-reactive if it binds to an epitope other than the one that induced its formation, e.g., various different ebolavirus internal fusion loop regions. The cross-reactive epitope contains many of the same complementary structural features as the inducing epitope, and in some cases, can actually fit better than the original.

A pan-ebolavirus internal fusion loop antibody or fragment, variant, or derivative thereof can also be described or specified in terms of their binding affinity to an antigen. For example, an antibody can bind to an antigen with a dissociation constant or $K_D$ no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $1011$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibody fragments including single-chain antibodies can comprise the variable region(s) alone or in combination with the entirety or a portion of the following: hinge region, CH1, CH2, and CH3 domains. Also included are antigen-binding fragments that comprise any combination of variable region(s) with a hinge region, CH1, CH2, and CH3 domains. Binding molecules, e.g., antibodies, or antigen-binding fragments thereof disclosed herein can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain, a pan-ebolavirus internal fusion loop antibody or antigen-binding fragment thereof comprising a heavy chain portion comprises at least one of: a CH1 domain, a hinge (e.g., upper, middle, and/or lower hinge region) domain, a CH2 domain, a CH3 domain, or a variant or fragment thereof. For example, a pan-ebolavirus internal fusion loop antibody or fragment, variant, or derivative thereof can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a pan-ebolavirus internal fusion loop antibody or fragment, variant, or derivative thereof comprises a polypeptide chain comprising a CH3 domain. Further, a pan-ebolavirus internal fusion loop antibody for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

The heavy chain portions of a pan-ebolavirus internal fusion loop antibody or antigen-binding fragment thereof as disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion comprises at least one of a VL or CL domain.

Pan-ebolavirus internal fusion loop antibodies, e.g., antibodies or antigen-binding fragments, variants, or derivatives thereof disclosed herein can be described or specified in terms of the epitope(s) or portion(s) of an antigen, e.g., a target ebolavirus glycoprotein subunit that they recognize or specifically bind. The portion of a target antigen that specifically interacts with the antigen-binding domain of an antibody is an "epitope," or an "antigenic determinant." A target antigen, e.g., an ebolavirus glycoprotein subunit can comprise a single epitope, but typically comprises at least two epitopes, and can include any number of epitopes, depending on the size, conformation, and type of antigen. As used herein, an "orthologous epitope" refers to versions of an epitope found in related organisms, e.g., different ebolavirus species or strains. Orthologous epitopes can be similar in structure, but can vary in one or more amino acids.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about amino acid 244 to amino acid 360 of an antibody using conventional numbering schemes (amino acids 244 to 360, Kabat numbering system; and amino acids 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 amino acids.

As used herein, the term "hinge region" includes the portion of a heavy chain molecule that joins the CH1 domain to the CH2 domain. This hinge region comprises approximately 25 amino acids and is flexible, thus allowing the two N-terminal antigen-binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more CDRs from an antibody of known specificity and, by partial framework region replacement and sequence changing. Although the CDRs can be derived from an antibody of the same class or even subclass as the antibody from which the framework regions are derived, it is envisaged that the CDRs will be derived from an antibody of different class, e.g., from an antibody from a different species. An engineered antibody in which one or more "donor" CDRs from a non-human antibody of known specificity is grafted into a human heavy or light chain framework region is referred to herein as a "humanized antibody." In some instances, not all of the CDRs are replaced with the complete CDRs from the donor variable region to transfer the antigen binding capacity of one variable domain to another, instead, minimal amino acids that maintain the activity of the target-binding site are transferred. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that could be at any time, determined or interpreted by a judge or an administrative or judicial body to be, "naturally-occurring."

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide as disclosed herein, e.g., a polynucleotide encoding a polypeptide subunit provided herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness. The term "protection" and related grammatical terms, when used in the context of the ability of a therapeutic agent to affect the course of an infectious disease refers to any protective effect observed in comparison to a control agent. For example if two groups of animals are challenged with an infectious agent, e.g., a lethal dose of EBOV, and one group of animals is administered the therapeutic agent while the other group is administered a control, if a statistically significant number of animals in the therapeutic group survive relative to the number of survivors in the control group, a protective effect is observed. "Protection" can be, but does not have to be, 100%.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on. "A subject in need of treatment" refers to a subject that can benefit from a treatment with a particular composition, e.g., to prevent or treat a disease.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

Certain therapies can provide "synergy" and prove "synergistic", i.e., an effect can be achieved when the active ingredients used together that is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

Pan-Ebolavirus Internal Fusion Loop Antibodies. This disclosure provides a pan-ebolavirus internal fusion loop (IFL) antibody or antigen-binding fragment thereof. Pan-ebolavirus internal fusion loop antibodies or antigen-binding fragments can be useful for treatment of an ebolavirus infection without it being necessary to know the exact ebolavirus species or strain. More specifically, the disclosure provides an isolated antibody or antigen-binding fragment thereof comprising a binding domain that specifically binds to an orthologous ebolavirus IFL glycoprotein epitope, wherein the binding domain specifically binds to the epitope on two, three, four, five, or more ebolavirus species or strains. In certain aspects the antibody can be bispecific.

In certain aspects, the binding domain of a pan-ebolavirus internal fusion loop antibody or antigen-binding fragment thereof can specifically bind to an ebolavirus orthologous epitope as expressed in two or more, three or more, four or more, or five or more ebolavirus species including, Tai Forest ebolavirus (TAFV), Reston ebolavirus (RESTV), Sudan ebolavirus (SUDV), Ebola virus (EBOV), Bundibugyo ebolavirus (BDBV), or any strain of any of these ebolavirus species. For example, the binding domain of a pan-ebolavirus internal fusion loop antibody or antigen-binding fragment thereof can bind to an orthologous ebolavirus epitope as expressed in two or more, three or more, four or more, or five of EBOV, SUDV, RESTV, and BDBV.

An exemplary binding domain can be derived from the VH and VL antigen binding domains of non-human primate antibody CA45, which binds to the ebolavirus GP IFL across four different species of ebolavirus, EBOV, SUDV, RESTV, and BDBV. In certain aspects the binding domain of this exemplary pan-ebolavirus internal fusion loop antibody or antigen-binding fragment thereof can bind to the same orthologous epitope as an antibody or antigen-binding fragment thereof comprising a heavy chain variable region (VH) and light chain variable region (VL) comprising, respectively, the amino acid sequences SEQ ID NO: 1 and SEQ ID NO: 2.

In certain aspects a pan-ebolavirus internal fusion loop antibody or antigen-binding fragment thereof as provided herein can be capable of functioning at the pH found in endosomal compartments of ebolavirus infected cells, e.g., at an acidic pH For example in certain aspects a binding domain of a pan-ebolavirus internal fusion loop antibody or antigen-binding fragment thereof as provided herein can bind to an orthologous ebolavirus IFL epitope in solution at a pH of about 4.0, about 4.5, about 5.0, about 5.5, about 6.0, about 6.5, about 7.0, or about 7.5.

In certain aspects the disclosure provides a pan-ebolavirus internal fusion loop antibody or antigen-binding fragment thereof comprising a binding domain that comprises CDRH1, CDRH2, CDRH3, CDRL1, CDRL2, and CDRL3 amino acid sequences identical or identical except for four, three, two, or one single amino acid substitutions, deletions, or insertions in one or more CDRs to: SEQ ID NOs:3, 4, 5, 6, 7, and 8; respectively. In certain aspects, CDRH1 comprises SEQ ID NO: 3 or SEQ ID NO: 3 with one or two single amino acid substitutions, wherein the substitutions are at positions X1 and/or X2 of G-Y-Y-X1-W-X2 (SEQ ID NO: 9); CDRH2 comprises SEQ ID NO: 4, or SEQ ID NO: 4 with one, two, or three single amino acid substitutions; CDRH3 comprises SEQ ID NO: 5 or SEQ ID NO: 5 with one, two, or three single amino acid substitutions, wherein the substitutions are at positions X1, X2, X3, X4, X5, X6, X7, X8, X9, X10, X11, and/or X12 of D-X1-G-X2-T-I-F-X3-X4-X5-I-X6-X7-W-X8-X9-X10-D-X12 (SEQ ID NO: 10); CDRL1 comprises SEQ ID NO: 6, or SEQ ID NO: 6 with one, two, or three single amino acid substitutions; CDRL2 comprises SEQ ID NO: 7, or SEQ ID NO: 7 with one, two, or three single amino acid substitutions; and CDRL3 comprises SEQ ID NO: 8, or SEQ ID NO: 8 with one, two, or three single amino acid substitutions.

Furthermore, in certain aspects the disclosure provides a pan-ebolavirus internal fusion loop antibody or antigen-binding fragment thereof comprising a first binding domain that comprises VH and VL amino acid sequences at least 85%, 90%, 95%, or 100% identical to reference amino acid sequences SEQ ID NO: 1 and SEQ ID NO: 2, respectively.

A pan-ebolavirus internal fusion loop antibody or antigen-binding fragment thereof as provided herein can be, e.g., a human antibody, a murine antibody, a non-human primate antibody, a humanized antibody, a chimeric antibody, or any fragment thereof. Moreover, the antibody or fragment thereof can be a monoclonal antibody, a component of a polyclonal antibody mixture, a recombinant antibody, a multispecific antibody, or any combination thereof.

In certain aspects, a pan-ebolavirus internal fusion loop antibody or antigen-binding fragment thereof as provided herein can be a bispecific antibody or fragment thereof that further comprises a second binding domain. In certain aspects, a second binding domain can bind to a surface exposed epitope on a virion particle, for example, the second binding domain can specifically bind to an epitope located in the receptor binding domain, the mucin-like domain, an epitope located in the glycan cap, an additional epitope located in the GP2 fusion domain, or any combination thereof.

An antibody or fragment thereof of as provided herein can in certain aspects comprise a heavy chain constant region or fragment thereof. The heavy chain can be a murine constant region or fragment thereof, e.g., a human constant region or fragment thereof, e.g., IgM, IgG, IgA, IgE, IgD, or IgY constant region or fragment thereof. Various human IgG constant region subtypes or fragments thereof can also be included, e.g., a human IgG1, IgG2, IgG3, or IgG4 constant region or fragment thereof.

An antibody or fragment thereof as provided herein can further comprise a light chain constant region or fragment thereof. For example, the light chain constant region or fragment thereof can be a murine constant region or fragment thereof, e.g., a human light chain constant region or fragment thereof, e.g., a human kappa or lambda constant region or fragment thereof.

In certain aspects the binding domain of a pan-ebolavirus internal fusion loop antibody or antigen-binding fragment thereof as provided herein comprises a full-size antibody comprising two heavy chains and two light chains. In other aspects, the binding domain of a pan-ebolavirus internal fusion loop antibody or antigen-binding fragment thereof as provided herein comprises an Fv fragment, an Fab fragment, an F(ab')2 fragment, an Fab' fragment, a dsFv fragment, an scFv fragment, an scFab fragment, an sc(Fv)2 fragment, or any combination thereof.

In certain aspects a pan-ebolavirus internal fusion loop antibody or antigen-binding fragment thereof as provided herein can fully or partially neutralize infectivity of the ebolavirus upon binding of the binding domain to the orthologous epitope on an ebolavirus.

In certain aspects, a pan-ebolavirus internal fusion loop antibody or antigen-binding fragment thereof as provided herein can be conjugated to an antiviral agent, a protein, a lipid, a detectable label, a polymer, or any combination thereof.

The disclosure further provides a composition comprising a pan-ebolavirus internal fusion loop antibody or antigen-binding fragment thereof, and a carrier.

Polynucleotides

In certain aspects the disclosure provides an isolated polynucleotide comprising a nucleic acid encoding a pan-ebolavirus internal fusion loop antibody or antigen-binding fragment thereof or a subunit thereof. For example, a polynucleotide as provided herein can include a nucleic acid encoding a VH, wherein the VH comprises a CDRH1, a CDRH2, and a CDRH3, wherein CDRH1 comprises SEQ ID NO: 3 or SEQ ID NO: 3 with one or two single amino acid substitutions, wherein the substitutions are at positions X1 and/or X2 of G-Y-Y-X1-W-X2 (SEQ ID NO: 9); wherein CDRH2 comprises SEQ ID NO: 4, or SEQ ID NO: 4 with one, two, or three single amino acid substitutions; and wherein CDRH3 comprises SEQ ID NO: 5 or SEQ ID NO: 5 with one, two, or three single amino acid substitutions, wherein the substitutions are at positions X1, X2, X3, X4, X5, X6, X7, X8, X9, X10, X11, and/or X12 of D-X1-G-X2-T-I-F-X3-X4-X5-I-X6-X7-W-X8-X9-X10-D-X12 (SEQ ID NO: 10).

Moreover, a polynucleotide as provided herein can include a nucleic acid encoding a VL that includes a CDRL1, a CDRL2, and a CDRL3, wherein CDRL1 comprises SEQ ID NO: 6, or SEQ ID NO: 6 with one, two, or three single amino acid substitutions; wherein CDRL2 comprises SEQ ID NO: 7, or SEQ ID NO: 7 with one, two, or three single amino acid substitutions; and wherein CDRL3 comprises SEQ ID NO: 8, or SEQ ID NO: 8 with one, two, or three single amino acid substitutions.

In certain aspects, a polynucleotide as provided herein an include a nucleic acid encoding a VH that comprises an amino acid sequence at least 85%, 90%, 95%, or 100% identical to the reference amino acid sequence SEQ ID NO: 1. In certain aspects, a polynucleotide as provided herein an include a nucleic acid encoding a VL, wherein the VL comprises an amino acid sequence at least 85%, 90%, 95%, or 100% identical to the reference amino acid sequence SEQ ID NO: 2.

The disclosure further provides a vector comprising a polynucleotide as provided herein, and a composition comprising a polynucleotide or a vector as provided herein.

In certain aspects the disclosure provides a polynucleotide or a combination of polynucleotides encoding a pan-ebolavirus internal fusion loop antibody or antigen-binding fragment thereof. In certain aspects the polynucleotide or combination of polynucleotides can comprise a nucleic acid encoding a VH, and a nucleic acid encoding a VL, wherein the VH and VL comprise CDRH1, CDRH2, CDRH3, CDRL1, CDRL2, and CDRL3 amino acid sequences identical or identical except for four, three, two, or one single amino acid substitutions, deletions, or insertions in one or more CDRs to: SEQ ID NOs: 3, 4, 5, 6, 7, and 8; respectively. In certain aspects CDRH1 comprises SEQ ID NO: 3 or SEQ ID NO: 3 with one or two single amino acid substitutions, wherein the substitutions are at positions X1 and/or X2 of G-Y-Y-X1-W-X2 (SEQ ID NO: 9); CDRH2 comprises SEQ ID NO: 4, or SEQ ID NO: 4 with one, two, or three single amino acid substitutions; CDRH3 comprises SEQ ID NO: 5 or SEQ ID NO: 5 with one, two, or three single amino acid substitutions, wherein the substitutions are at positions X1, X2, X3, X4, X5, X6, X7, X8, X9, X10, X11, and/or X12 of D-X1-G-X2-T-I-F-X3-X4-X5-I-X6-X7-W-X8-X9-X10-D-X12 (SEQ ID NO: 10); CDRL1 comprises SEQ ID NO: 6, or SEQ ID NO: 6 with one, two, or three single amino acid substitutions; CDRL2 comprises SEQ ID NO: 7, or SEQ ID NO: 7 with one, two, or three single amino acid substitutions; and CDRL3 comprises SEQ ID NO: 8, or SEQ ID NO: 8 with one, two, or three single amino acid substitutions.

In certain aspects the polynucleotide or combination of polynucleotides can comprise a nucleic acid encoding a VH, and a nucleic acid encoding a VL, wherein the VH and VL comprise amino acid sequences at least 85%, 90%, 95%, or 100% identical to reference amino acid sequences SEQ ID NO: 1 and SEQ ID NO: 2, respectively.

In certain aspects of the polynucleotide or combination of polynucleotides as provided herein the nucleic acid encoding a VH and the nucleic acid encoding a VL can be in the same vector. Such a vector is also provided.

In certain aspects of the polynucleotide or combination of polynucleotides as provided herein the nucleic acid encoding a VH and the nucleic acid encoding a VL can be in different vectors. Such vectors are further provided.

The disclosure also provides a host cell comprising the polynucleotide or combination of polynucleotides as provided herein or the vector or vectors as provided.

Moreover, the disclosure provides a method of making a pan-ebolavirus internal fusion loop antibody or antigen-binding fragment thereof, comprising culturing a host cell as provided; and isolating the antibody or fragment thereof.

In certain embodiments, the polynucleotides comprise the coding sequence for the mature pan-ebolavirus internal fusion loop antibody or antigen-binding fragment thereof, fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) can be used.

Polynucleotide variants are also provided. Polynucleotide variants can contain alterations in the coding regions, non-coding regions, or both. In some embodiments polynucleotide variants contain alterations that produce silent substitutions, additions, or deletions, but do not alter the properties or activities of the encoded polypeptide. In some embodiments, polynucleotide variants can be produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some embodiments, a DNA sequence encoding pan-ebolavirus internal fusion loop antibody or antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors are used to amplify and express DNA encoding a pan-ebolavirus internal fusion loop antibody or antigen-binding fragment thereof. Recombinant expression vectors are replicable DNA constructs which have synthetic or cDNA-derived DNA fragments encoding a polypeptide chain of an anti-ebolavirus antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine. This methionine can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of a pan-ebolavirus internal fusion loop antibody or antigen-binding fragment thereof include prokaryotes, yeast, insect or higher eukaryotic cells under the control of appropriate promoters. Prokaryotes include gram negative or gram-positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be employed to express a pan-ebolavirus internal fusion loop antibody or antigen-binding fragment thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

A pan-ebolavirus internal fusion loop antibody or antigen-binding fragment thereof produced by a transformed host, can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a pan-ebolavirus internal fusion loop antibody or antigen-binding fragment thereof. Some or all of the foregoing purification steps, in various combinations, can also be employed to provide a homogeneous recombinant protein.

A pan-ebolavirus internal fusion loop antibody or antigen-binding fragment thereof produced in bacterial culture, can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

Methods of Treatment

This disclosure provides methods for treating, preventing, ameliorating or suppressing symptoms of ebolavirus infection, e.g., EBOV, SUDV, BDBV, or RESTV infection comprising administering to a subject in need thereof pan-ebolavirus internal fusion loop antibody or antigen-binding fragment thereof as provided herein. In certain aspects the method includes administering two, three, four, five or more of such antibodies to, e.g., improve efficacy, reduce the number of treatments, to allow efficacy when administered at a later time from the inception of infection in the subject, and/or to allow dose sparing. In certain aspects administration of two or more antibodies as a combination therapy can result in synergistic efficacy, e.g., efficacy that is more potent than would be expected based on the efficacy of the antibodies administered individually. Pan-ebolavirus antibodies, e.g., pan-ebolavirus internal fusion loop antibodies as provided herein, as well as combinations thereof can be useful for treatment of an ebolavirus infection without it being necessary to know the exact ebolavirus species or strain. More specifically, the disclosure provides methods of using an isolated pan-ebolavirus internal fusion loop antibody or antigen-binding fragment thereof comprising a binding domain that specifically binds to an orthologous ebolavirus glycoprotein IFL epitope, wherein the binding domain specifically binds to the epitope on two, three, four, five, or more ebolavirus species or strains. In certain aspects, the disclosure further provides such orthologous ebolavirus glycoprotein IFL epitopes. In certain aspects the pan-ebolavirus internal fusion loop antibody as provided herein can be a cross-reactive antibody or antigen-binding fragment thereof. In certain aspects the antibody can be a bispecific antibody.

In certain aspects, the binding domain of a pan-ebolavirus internal fusion loop antibody or antigen-binding fragment thereof for use in the methods provided herein can specifically bind to an ebolavirus orthologous epitope as expressed in one or more, two or more, three or more, four or more, or five or more ebolavirus species or strains thereof, including, without limitation, Tai Forest ebolavirus (TAFV), Reston ebolavirus (RESTV), Sudan ebolavirus (SUDV), Ebola virus (EBOV), and Bundibugyo ebolavirus (BDBV). For example, the binding domain of a pan-ebolavirus internal fusion loop antibody or antigen-binding fragment thereof for use in the methods provided herein can bind to an orthologous ebolavirus epitope as expressed in one or more, two or more, or three of EBOV, SUDV, RESTV, TAFV, and BDBV. In certain aspects, the binding domain of a pan-ebolavirus internal fusion loop antibody or antigen-binding fragment thereof for use in the methods provided herein can bind to an orthologous ebolavirus epitope as expressed in EBOV, SUDV, BBDB, and RESTV.

In certain aspects the orthologous epitope comprises, or is situated on, in, or within the internal fusion loop region of GP2. For example the orthologous epitope can, in some aspects, be contained within discontinuous consensus sequences in GP2 that include or comprise Y517 in beta sheet β19 and G546 and N550 in beta sheet β20. In certain aspects, the orthologous further comprises the associated GP1 amino acid R/K64 in beta sheet β3 (see, e.g., FIG. 4C).

Methods are provided for the use of pan-ebolavirus internal fusion loop antibodies, e.g., cross-reactive anti-ebolavirus antibodies or fragments thereof, to treat patients having a disease or condition associated with an ebolavirus infection, or to prevent, reduce, or manage ebolavirus-induced virulence in a subject infected with an ebolavirus.

The following discussion refers to methods of treatment of various diseases and disorders with a pan-ebolavirus internal fusion loop antibody or antigen-binding fragment thereof that retains the desired properties of anti-ebolavirus antibodies provided herein, e.g., capable of specifically binding to and neutralizing ebolavirus infectivity and/or virulence. In some embodiments, a pan-ebolavirus internal fusion loop antibody or antigen-binding fragment thereof for use in the methods provided herein can be a murine, human, non-human primate, or humanized antibody. In some embodiments, the pan-ebolavirus internal fusion loop antibody or antigen-binding fragment thereof comprises a binding domain that binds to the same epitope as, or competitively inhibits binding of, monoclonal antibody CA45, as provided herein. In some embodiments, the binding domain of a pan-ebolavirus internal fusion loop antibody or antigen-binding fragment thereof as provided herein is derived from monoclonal antibody CA45 as provided herein. In certain embodiments the binding domain of the derived antibody is an affinity-matured, chimeric, or humanized antibody.

In one embodiment, treatment includes the application or administration of a pan-ebolavirus internal fusion loop antibody or antigen-binding fragment thereof as provided herein, to a subject or patient, where the subject or patient has been exposed to an ebolavirus, infected with an ebolavirus, has an ebolavirus disease, a symptom of an ebolavirus disease, or a predisposition toward contracting an ebolavirus disease. In another embodiment, treatment can also include the application or administration of a pharmaceutical composition comprising a pan-ebolavirus internal fusion loop antibody or antigen-binding fragment thereof as provided herein, to a subject or patient, so as to target the pharmaceutical composition to an environment where the pan-ebolavirus internal fusion loop antibody can be most effective, e.g., the endosomal region of a virus-infected cell.

In accordance with the methods of the present disclosure, at least one pan-ebolavirus internal fusion loop antibody or antigen-binding fragment thereof as defined elsewhere herein can be used to promote a positive therapeutic response. By "positive therapeutic response" is intended any improvement in the disease conditions associated with the activity of the pan-ebolavirus internal fusion loop antibody or antigen-binding fragment thereof, and/or an improvement in the symptoms associated with the disease. Thus, for example, an improvement in the disease can be characterized as a complete response. By "complete response" is intended an absence of clinically detectable disease with normalization of any previously test results. Such a response can in some cases persist, e.g., for at least one month following treatment according to the methods of the disclosure. Alternatively, an improvement in the disease can be categorized as being a partial response.

Treatment Methods Using Cocktails of Cross-Reactive Anti-Ebolavirus Antibodies

Mounting evidence suggests that cocktails of two or more anti-ebolavirus glycoprotein antibodies, e.g., anti-EBOV, SUDV, or MARV GP antibodies, can provide life-sustaining benefit to subjects, e.g., patients and/or healthcare workers exposed to or susceptible to exposure to, ebolavirus infection, e.g., EBOV, SUDV, BDBV, or RESTV. At the initiation of an outbreak or infection, the exact species or strain of ebolavirus might not be immediately determined, or the outbreak could be caused by more than one ebolavirus species or strain. Accordingly, this disclosure provides methods for preventing, treating, and/or managing ebolavirus infections or outbreaks using cocktails comprising a pan-ebolavirus internal fusion loop antibody or antigen-binding fragment thereof as provided herein and one or more additional ebolavirus GP antibodies, where the cocktail can be effective against more than one ebolavirus species or strain.

In certain aspects, this disclosure provides a method for preventing, treating, or managing a ebolavirus infection in a subject where the method entails administering to a subject in need thereof an effective amount of an antibody cocktail that includes, or comprises, at least two antibodies or antigen-binding fragment thereof that specifically bind to different epitopes on a ebolavirus glycoprotein (ebolavirus GP), including a pan-ebolavirus internal fusion loop antibody or antigen-binding fragment thereof as provided herein. In certain aspects, at least one antibody or fragment thereof in the cocktail, e.g., a pan-ebolavirus internal fusion loop antibody or antigen-binding fragment thereof as provided herein can specifically bind to its orthologous epitope on two or more ebolavirus species or strains. In other words, if the antibody or fragment thereof was raised against the EBOV glycoprotein and is found to bind to the EBOV internal fusion loop, the antibody "can specifically bind to its orthologous epitope on two or more ebolavirus species or strains" if the antibody or fragment thereof also binds to, e.g., the internal fusion loop of other strains of EBOV and/or the TAFV, RESTV, SUDV, and/or BDBV internal fusion loop, or any strain thereof. Moreover, in certain aspects, administration of the antibody cocktail can be effective against two or more ebolavirus species or strains, e.g., the antibody cocktail can neutralize two or more ebolavirus species or strains and/or protect against disease caused by two or more ebolavirus species or strains, e.g., in an animal challenge model. The two or more ebolavirus species can be two or more of Tai Forest virus (TAFV), Reston virus (RESTV), Sudan virus (SUDV) Ebola virus (EBOV), Bundibugyo virus (BDBV), or any strain thereof. In certain aspects, the ebolavirus infection is hemorrhagic fever. In certain aspects, the subject is a nonhuman primate or a human.

In certain aspects the antibodies or fragments thereof for use in the methods provided herein can each independently be, e.g., a mouse antibody, a non-human primate (NHP) antibody, a humanized antibody, a chimeric antibody, or a fragment thereof. Moreover, the antibody or fragment thereof can be a monoclonal antibody, a component of a polyclonal antibody mixture, a recombinant antibody, a multispecific antibody, or any combination thereof.

In certain aspects, the ability of the antibody cocktail to prevent, treat, or manage a ebolavirus infection, and or the potency relative to individual antibodies, can be measured in a model comprising administering the antibody cocktail to a group of mammals, e.g., mice, guinea pigs, or ferrets, and challenging animals with wild type or species-adapted (e.g., mouse adapted or guinea pig adapted) ebolavirus before, at the same time as, or after administering the antibody cocktail to the animals. In any such animal model, the challenged animals can be monitored for increased survival time, decreased weight loss, or a combination thereof as compared to control animals. In other aspects the ability of the antibody cocktail to prevent, treat, or manage a ebolavirus infection, and or the potency relative to individual antibodies, can be measured in a neutralization assay as described elsewhere herein.

In certain aspects of the provided method, the subject is administered an effective amount of an antibody cocktail as described above. In certain aspects, the antibody cocktail can prevent, treat, or manage ebolavirus infection in the subject with a potency that is greater than the additive potency of the antibodies or fragments thereof when administered individually.

In certain aspects, administration of the provided antibody cocktail to the subject is effective against two or more ebolavirus species or strains. In certain aspects the method includes administering the antibody cocktail to, e.g., improve efficacy, reduce the number of treatments, to allow efficacy when administered at a later time from the inception of infection in the subject, and/or to allow dose sparing. In certain aspects administration of the antibody cocktail can result in synergistic efficacy, e.g., efficacy that is more potent than would be expected based on the efficacy of the antibodies administered individually. Moreover, the antibody cocktails provided herein can be useful for treatment of an ebolavirus infection without it being necessary to know the exact ebolavirus species or strain. Any antibody cocktail described herein can include, in addition to the recited antibodies, other antibodies that bind to the same or different ebolavirus glycoprotein epitopes.

In certain aspects each antibody or fragment thereof of an antibody cocktail for use in the methods provided herein can independently comprise a heavy chain constant region or fragment thereof. The heavy chain can be, e.g., a murine constant region or fragment thereof, a human constant region or fragment thereof, e.g., an IgM, IgG, IgA, IgE, IgD, or IgY constant region or fragment thereof. Various human IgG constant region subtypes or fragments thereof can also be included, e.g., a human IgG1, IgG2, IgG3, or IgG4 constant region or fragment thereof.

In certain aspects each antibody or fragment thereof of an antibody cocktail for use in the methods provided herein can independently further comprise a light chain constant region or fragment thereof. For example, the light chain constant region or fragment thereof can be a murine constant region or fragment thereof, e.g., a human light chain constant region or fragment thereof, e.g., a human kappa or lambda constant region or fragment thereof.

In certain aspects each antibody or fragment thereof of an antibody cocktail for use in the methods provided herein can independently comprise a full-size antibody comprising two heavy chains and two light chains. In other aspects, the binding domain(s) of each antibody or fragment thereof of an antibody cocktail for use in the methods provided herein can independently be an Fv fragment, an Fab fragment, an F(ab')2 fragment, an Fab' fragment, a dsFv fragment, an scFv fragment, an scFab fragment, an sc(Fv)2 fragment, or any combination thereof.

In certain aspects each antibody or fragment thereof of an antibody cocktail for use in the methods provided herein can, either independently or collectively, fully or partially neutralize infectivity of an ebolavirus upon binding of the binding domain to one or more orthologous epitopes on the ebolavirus.

In certain aspects, each antibody or fragment thereof of an antibody cocktail for use in the methods provided herein can independently be conjugated to an antiviral agent, a protein, a lipid, a detectable label, a polymer, or any combination thereof.

In certain aspects the antibody cocktail includes, in addition to a pan-ebolavirus internal fusion loop antibody or antigen-binding fragment thereof as provided herein, at least a second anti-ebolavirus GP antibody or antigen-binding fragment thereof. According to one aspect the second antibody or fragment thereof can specifically bind to, e.g., an ebolavirus GP1/GP2 base epitope, an ebolavirus GP receptor binding site (RBS) epitope, an ebolavirus GP glycan cap epitope, an additional ebolavirus GP internal fusion loop (IFL) epitope, or any combination thereof. Antibodies binding to the base epitope include, without limitation, 2G4, 4G7, and/or ADI-15734, described, e.g., in PCT Publication No. WO 2015/200522 and U.S. Provisional Appl. No. 62/368,688 (Bornholdt, et al., 2016, Science, 351(6277): 1078-83; Murin, et al., 2014, Proc Natl Acad Sci US A, 111(48):17182-7). Antibodies that bind to the RBS epitope include, without limitation, FVM04 (described elsewhere herein and in, e.g., PCT Publication No. WO 2016/069627), and MR191, described, e.g., in U.S. Provisional Appl. No. 62/368,688, and mAb114 described, e.g., in (ref for FVM04: Keck, et al., 2015, J Virol, 90:279-291; and Howell et al. 2016, Cell Reports, 15, 1514-1526; for mAb 114: Corti et al. 2016, Science, 351(6279):1339-42; for MR191 Flyak et al. 2015, Cell, 160(5):904-12). Antibodies that bind to the glycan cap epitope include, without limitation, 13C6FR1, FVM09, ADI-15731, m8C4 (in part), and ADI-15750 (in part), described, e.g., in U.S. Provisional Appl. No. 62/368, 688, and mAb 114 (in part) (Reference for the antibodies: for 2G4 and 4G7: Murin, et al., 2014, Proc Natl Acad Sci USA, 111(48):17182-7; for FVM04: Keck, et al., 2015, J Virol, 90:279-291; For Adi-15570: Bornholdt, et al., 2016, Science, 351(6277): 1078-83; for m8C4: Holtsberg, et al., 2015, J Virol, 90:266-278; for mAb 114: Corti et al. 2016, Science, 351(6279):1339-42). Antibodies binding to the IFL epitope in addition to the CA45 antibody described herein include, without limitation, FVM02 (Keck, et al., 2015, J Virol, 90:279-291), ADI-15742, ADI-15878, and ADI-15946 (Bornholdt, et al., 2016, Science, 351(6277):1078-83), described, e.g., in U.S. Provisional Appl. No. 62/368,688 and mAb100 described in Corti et al. 2016, Science, 351 (6279):1339-42).

In accordance with the methods of the present disclosure, an antibody cocktail as provided herein can be used to promote a positive therapeutic response. By "positive therapeutic response" is intended any improvement in the disease conditions associated with the activity of the antibody cocktail, and/or an improvement in the symptoms associated with the disease. Thus, for example, an improvement in the disease can be characterized as a complete response. By "complete response" is intended an absence of clinically detectable disease with normalization of any previously test results. Such a response can in some cases persist, e.g., for at least one month following treatment according to the methods of the disclosure. Alternatively, an improvement in the disease can be categorized as being a partial response.

Pharmaceutical Compositions and Administration Methods

Methods of preparing and administering a pan-ebolavirus internal fusion loop antibody or antigen-binding fragment thereof provided herein, or an antibody cocktail as provided herein, to a subject in need thereof are well known to or are readily determined by those skilled in the art. The route of administration of a pan-ebolavirus internal fusion loop antibody or antigen-binding fragment thereof, or an antibody cocktail comprising the antibody, for use in the methods provided herein can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as suitable forms, another example of a form for administration would be a solution for injection, in particular for intravenous or intraarterial injection or drip. In some cases a suitable pharmaceutical composition can comprise a buffer (e.g. acetate, phosphate or citrate buffer), a surfactant (e.g. polysorbate), optionally a stabilizer agent (e.g. human albumin), etc. In other methods compatible with the teachings herein, a pan-ebolavirus internal fusion loop antibody or antigen-binding fragment thereof as provided herein, or an antibody cocktail as provided herein, can be delivered directly to a site where the antibody or antibody cocktail can be effective in virus neutralization, e.g., the endosomal region of an ebolavirus-infected cell.

As discussed herein, a pan-ebolavirus internal fusion loop antibody or antigen-binding fragment thereof provided herein, or an antibody cocktail as provided herein, can be administered in a pharmaceutically effective amount for the in vivo treatment of diseases or disorders associated with ebolavirus infection. In this regard, it will be appreciated that the disclosed antibody or antibody cocktail can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a pan-ebolavirus internal fusion loop antibody or antigen-binding fragment thereof, or an antibody cocktail comprising the antibody, means an amount sufficient to achieve effective binding to a target and to achieve a benefit, e.g., to ameliorate symptoms of a disease or condition or to detect a substance or a cell. Suitable formulations for use in the therapeutic methods disclosed herein can be described in Remington's Pharmaceutical Sciences (Mack Publishing Co.) 16th ed. (1980).

The amount of a pan-ebolavirus internal fusion loop antibody or antigen-binding fragment thereof or an antibody cocktail comprising the antibody that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide an optimum response (e.g., a therapeutic or prophylactic response).

In keeping with the scope of the present disclosure, a pan-ebolavirus internal fusion loop antibody or antigen-binding fragment thereof or an antibody cocktail for use in the methods provided herein can be administered to a human or other animal in accordance with the aforementioned methods of treatment in an amount sufficient to produce a therapeutic effect. A pan-ebolavirus internal fusion loop antibody or antigen-binding fragment thereof provided herein, or an antibody cocktail as provided herein, can be administered to such human or other animal in a conventional dosage form prepared by combining the antibody or antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of pan-ebolavirus internal fusion loop antibody or antigen-binding fragment thereof, or antibody cocktail, that when administered brings about a positive therapeutic response with respect to treatment of a patient with a disease or condition to be treated.

Therapeutically effective doses of the compositions disclosed herein, for treatment of diseases or disorders associated with ebolavirus infection, vary depending upon many different factors, including means of administration, target site, physiological state of the patient, whether the patient is human or an animal, other medications administered, and whether treatment is prophylactic or therapeutic. Usually, the patient is a human, but non-human mammals including non-human primates can also be treated. Treatment dosages can be titrated using routine methods known to those of skill in the art to optimize safety and efficacy.

The amount of a pan-ebolavirus internal fusion loop antibody or antigen-binding fragment thereof to be administered can be readily determined by one of ordinary skill in the art without undue experimentation given this disclosure. Factors influencing the mode of administration and the respective amount of pan-ebolavirus internal fusion loop antibody or antigen-binding fragment thereof include, but are not limited to, the severity of the disease, the history of the disease, and the age, height, weight, health, and physical condition of the individual undergoing therapy. Similarly, the amount of pan-ebolavirus internal fusion loop antibody or antigen-binding fragment thereof to be administered will be dependent upon the mode of administration and whether the subject will undergo a single dose or multiple doses of this agent.

This disclosure also provides for the use of pan-ebolavirus internal fusion loop antibody or antigen-binding fragment thereof in the manufacture of a medicament for treating, preventing, or managing a disease or disorder associated with ebolavirus infection, e.g., hemorrhagic fever.

EXAMPLES

Example 1: Isolation of the Monoclonal Antibody CA45

We used B cells from a cynomolgus macaque (Animal #20667; described in PCT Publication NO. WO 2016/069627 and Keck, et al., 2015, *J Virol*, 90:279-291) that was immunized 3 times with engineered trivalent filovirus glycoproteins (GP) consisting of EBOV/SUDV/MARV GPΔmuc. 28 days after the third immunizations (time point Week 12), the serum of monkey 20667 demonstrated moderate neutralization activity against three ebolaviruses EBOV, SUDV, BDBV (FIG. 1A), suggesting that ebolavirus cross-reactive B cells may exist in this animal. We sought to clone ebolavirus cross-reactive mAbs from the peripheral B cells of monkey 20667 by deploying a multicolor antigen-specific memory B cell fluorescence-activated cell sorting (FACS) and Ig cloning method that has been established and optimized recently for non-human primate B cell repertoire analysis (Sundling et al., Sci Transl Med 4, 142ra196).

We stained the peripheral blood mononuclear cells (PBMCs) of monkey 20667 after the third immunization using fluorescently labeled memory B cell surface marker cocktails along with GPΔmuc of EBOV and SUDV and sorted out cross-reactive surface IgG+ memory B cells. GP cross-reactive B cells with the phenotype of memory B cell (CD20+IgG+Aqua blue−CD14−CD3−CD8−CD27+IgM−) as well as dual GP reactivity (EBOV GPhi SDUV GPhi) (FIG. 1B) were sorted at single cell densities into individual wells of 96-well microtiter plates, followed by RT-PCR amplification of the Ig heavy- and light-chain cDNAs.

Among memory B cell compartment of the GP-immunized monkey 20667, about 0.5% memory B cells are GP-specific, with the frequency of cross-reactive GP-specific memory B cells is 0.06%, accounting for ~10% of GP-specific memory B cells. From $6 \times 10^6$ PBMCs, we sorted out 28 Ebola virus family GP cross-reactive memory B cells with 17 cells possessing paired HC/LC, among which we selected 12 of the clones to express full length IgG1 for ELISA assay. Over 90% of the clones ($^{11}/_{12}$) were found to bind both EBOV and SDUV GPΔmuc proteins strongly or moderately by ELISA, (FIG. 1C), which validated the precision of the sorting method. Analysis of the heavy- and light-chain variable regions (VH and VL, respectively) along with the heavy chain complementarity determining region 3 (CDRH3) of these clones revealed that some clones ($^{4}/_{11}$) were related to each other and/or to clones identified by phage display in our previous study (WO 2016/069627; Keck, et al., 2015, *J Virol* 90:279-291), while some clones ($^{7}/_{11}$) were identified as single member clones suggesting various degree of genetic diversities of the cross-reactive GP-specific B cell repertoire. Furthermore, ~30% of the GP-reactive clones ($^{4}/_{11}$) were found to neutralize either pseudotyped EBOV or SDUV with 1 clone of single member ($^{1}/_{11}$, <10% frequency), named CA45, was found to neutralize both EBOV and SUDV, and selected for further analysis. The VH and VL sequences of CA45 are shown in Table 2. The complementarity determining regions (CDRs) are bold and underlined, delineated by Kabat numbering system through IgBlast (on the world wide web at ncbi.nlm.nih.gov/igblast/).

TABLE 2

Sequence of Heavy and light variable domains.

| Antibody name | Heavy chain Variable Domain amino acid sequence ($V_H$) | Light chain Variable Domain amino acid sequence ($V_L$) |
|---|---|---|
| CA45 | QVQLQEWGEGLVKPSE TLSLTCAVYGGSIS GYYHWNWIRLPPG KGLEWIG NIDNSASTNYNPSLKT RVTISKDTSKNQISLK VRSLTAADTAVYYCAR DPG FTIFGVVITSWSGLDS WGQGAVVTVSS (SEQ ID NO: 1) | DIQMTQSPSSLSASVGDTVT ITCRASQSISNNLAWYQQRP RRAPQLLIYAASNLS GVPSRFSGSGSGTDFTLTIS SLQAEDFAAYYC QQHNTLPLTFGGGTKVEI (SEQ ID NO: 2) |

Example 2: Characterization of CA45

Binding of CA45 was further examined by ELISA using purified GP ectodomains (GPΔTM) for EBOV, SUDV, BDBV, and RESTV. Since filovirus receptor interactions and cellular fusion occurs in the acidic environment of endosomes we examined CA45 binding to GP at both acidic and neutral pH. As shown in FIG. 2A, CA45 bound strongly to GPΔTM of EBOV, SUDV, BDBV, and to a lesser extent to RESTV at both acidic and neutral pH. The strongest binding was observed for BDBV with $EC_{50}$ values ranging from 0.65 to 1.41 nM at different pH (FIG. 2A) and the weakest binding for RESTV with $EC_{50}$ values of 20-50 nM. For all four viruses the binding was slightly stronger at acidic pH. Upon entry by micropinocytosis ebolavirus GP is cleaved by cysteine cathepsins to yield a 19KD truncated GP1 associated with GP2 in which the receptor binding site (RB S) is exposed. Upon interaction with the endosomal receptor Nieman Pick C1 (NPC1), cleaved GP ($GP_{CL}$) mediates fusion with the endosomal membrane (Aman, 2016, MBio, 7, e00346-00316). Soluble $GP_{CL}$ can be produced in vitro by thermolysin treatment of GPΔTM (Hashiguchi et al, 2015, Cell 160(5):904-12). As shown in FIG. 2A, CA45 bound to $GP_{CL}$, about 23, 14, and 7 fold better than GPΔTM at pH of 7.5, 5.5, and 4.5 respectively. In contrast, no binding was observed to soluble GP (sGP), the product of unedited GP gene (residues 1-295 followed by a unique C-terminal tail). These data indicate that CA45 binding does not require mucin-like domain (MLD) or the glycan cap and that removal of these two domains reduces the constraints on CA45 binding.

We then tested the ability of CA45 to neutralize a replication competent recombinant vesicular stomatitis virus pseudotyped with filovirus GP and expressing GFP (rVSV-GP-GFP) (Howell et al. 2016, Cell Reports, 15, 1514-1526). As shown in FIG. 2B, CA45 effectively neutralized r-VSV expressing GP of EBOV, SUDV, BDBV, and to a lesser extent RESTV, but not TAFV and LLOV. To confirm that the neutralization results from inhibition of cellular entry, CA45 was also tested in a single round infection assay using a replication incompetent pseudotyped virus expressing luciferase (rVSV-Luc). CA45 showed strong cross-neutralization of EBOV, SUDV, and BDBV pseudotypes in this single round infection assay indicating that it is an inhibitor of cellular entry. To examine if CA45 can neutralize the form of EBOV that interacts with NPC1 and mediates membrane fusion we cleaved rVSV-GP viruses with thermolysin and purified the cleaved virus. Interestingly, CA45 neutralizing potency was towards rVSV expressing $GP_{CL}$ for EBOV, SUDV, and BDBV was drastically higher (100, 1900, and 600-fold reduction of $IC_{50}$ respectively) than those expressing wild type GP (FIG. 2B, right panel). This is consistent with stronger binding of CA45 to $GP_{CL}$, although the magnitude of increased potency is far more than what is expected from the binding data shown above.

Example 3: Identification of CA45 Residues Critical for GP Binding

The analysis of the VH and VL regions of CA45 revealed that it has the cynomolgus macaque germline IGHV4-21 and IGKV1-5, respectively (FIG. 3A), a 19-aa CDRH3 loop (FIG. 3A), and moderate level of somatic hypermutation (SHM, 9.9% nt and 14% aa for VH, and 7.5% nt and 14% aa for VK, respectively). Of note there is one amino acid deletion in the CDRH1 and the CDRH3 is flanked by two negatively charged residues $D^{95}$ and $D^{101}$, and contains eight residues of high hydrophobicity (Y,F,I,V,W, and L) (FIG. 3A), which may relate to important molecular recognition function. The gene family usage of CA45 was analyzed by IgBlast on the world wide web at ncbi.nlm.nih.gov/igblast/) with KABAT as the V domain delineation system.

To examine the molecular basis of CA45-GP interaction, we performed alanine scanning of CA45 CDRs and investigated the effect of the mutations in the CDRs on CA45 binding to EBOV GP (FIG. 3B), as well as SUDV and BDBV GPs (data not shown). Interestingly, only mutations in CDRH1 and CDRH3 cause dramatic decrease of CA45 binding to these three ebolavirus GPs (FIGS. 3B&C), while mutations in CDRH2 and all the light-chain CDRs have insignificant effect on CA45-GP binding (FIG. 3C). This implies that heavy chain of CA45 is directly involved in GP-recognition and light chain plays minor roles. Most of the residues in CDRH1 and CDRH3 that are critical for CA45-GP binding are either of highly hydrophobic (Y32, Y33, W35, F98, I100, F100a, I100e, W100 h), or negatively charged (D95 and D101) (FIG. 3C), suggesting that hydrophobic interactions and salt-bridges are heavily involved in the CA45-GP recognition interface.

Example 4: Epitope Mapping of CA45

To identify the critical GP residues required for CA45 binding we used an alanine scanning approach, where the binding of CA45 and two control antibodies was evaluated against a 'shotgun mutagenesis' mutation library of EBOV GP in which 641 of 644 GP residues were individually mutated. The method for shotgun mutagenesis is described in patent application 61/938,894 and (Davidson, E., and Doranz, B. J., 2014, Immunology, 143, 13-20). Human HEK-293T cells were transfected with the entire library in a 384-well array format and assessed for reactivity to CA45 by high-throughput flow cytometry (FIG. 4A). Two other macaque-derived GP antibodies FVM04 and FVM09 (PCT Publication No. WO 2016/069627; Keck, et al., 2015, J Virol, 90:279-291) were used as controls. FVM04 comprises the VH region amino acid sequence SEQ ID NO: 20, CDRH1, CDRH2, and CDRH3 amino acid sequences SEQ ID NO: 22, SEQ ID NO: 23, and SEQ ID NO: 24, respectively, the VL region amino acid sequence SEQ ID NO: 21, and CDRL1, CDRL2, and CDRL3 amino acid sequences SEQ ID NO: 25, SEQ ID NO: 26, and SEQ ID NO: 27, respectively. The epitope mapping identified EBOV GP residues R64 within the N-terminus of GP1 as well as Y517, G546, and N550 within the internal fusion loop (IFL) of GP2 as critical for CA45 binding (FIGS. 4A&B). Compared to wild type, alanine substitutions at these residues reduced CA45 binding to GP by 98%, 96%, 89%, and 78%, respectively, while the binding of FVM04 and FVM09 to these mutants was not reduced (FIG. 4B).

These residues are highly conserved among all ebolaviruses (FIG. 4C). R64 is located within the β3 strand at the N-terminus of EBOV GP and identical between Kikwit, Mayinga, and Makona strains of EBOV (SEQ ID NO: 11, SEQ ID NO: 12, and SEQ ID NO: 13, respectively). SUDV (e.g., SEQ ID NO: 14), BDBV (e.g., SEQ ID NO: 15), TAFV (e.g., SEQ ID NO: 16), and RESTV (e.g., SEQ ID NO: 17) have a lysine in this position. Y517 and G542 are positioned in beta strands β19 and β20 within the IFL and are identical among all ebolavirus species (FIG. 4C). N550 is located in the β20-α3 (HR1-A) loop and conserved among all filoviruses. In contrast except for the residues within β20 and β20-α3 loop marburgvirus GP (e.g., SEQ ID NO: 19 and SEQ ID NO: 19) shows little homology in this region (FIG. 4C). The key residues are positioned closely within the base of GP trimer (FIG. 4D). In addition to these four residues that reduced CA45 by >75%, it is noteworthy that alanine substitution of K191 that is positioned closely to the key residues (FIG. 4D) also reduced CA45 binding by 67% without affecting control antibody binding suggesting that K191 may also play a minor role in GP binding to CA45.

Example 5: In Vivo Protection Against EBOV and SUDV in Mice and Guinea Pigs

In vivo efficacy of CA45 as a post-exposure therapeutic was first tested in mouse models of EBOV and SUDV.

Groups of 10 BALB/c mice were infected with 100 pfu of mouse-adapted EBOV (MA-EBOV) (Bray, et al., 1999, *J Infect Dis.*, 179 Suppl 1, S248-258). Mice received a single intraperitoneal (IP) injection of CA45 at various doses, ranging from 10 to 0.5 mg/kg (200 to 10 jag/mouse), two days post infection (dpi). Control animals received PBS at 2 dpi. Highly significant protection from lethality was observed at all dose levels with P values of <0.0001 for doses above 1 mg/kg and 0.0119 for 0.5 mg/kg (FIG. 5A). Animals receiving CA45 showed reduced weight loss compared to PBS-treated mice with nearly no weight loss evident in mice treated with the highest dose of CA45 (FIG. 5A).

We then tested the efficacy of CA45 in a recently developed model of SUDV infection using mice deficient for IFNα/IFNβ receptor (IFNαβR$^{-/-}$; A129) (Brannan et al., 2015, *J Infect Dis.*, 212 Suppl 2:S282-94). Mice were challenged with 1000 pfu of wild type SUDV and treated by a single IP injection of antibody at 1 dpi. As shown in FIG. 5B, 10 mg/kg of CA45 protected 5 out of 6 animals from lethal infection and mice receiving CA45 exhibited an average of <6% weight loss compared to 28% for the PBS group. We had previously demonstrated partial protection against SUDV in this model using FVM04, an antibody that binds to the RBS and blocks interaction with NPC-1 (Howell et al. 2016, *Cell Reports*, 15, 1514-1526). We hypothesized that combining a receptor blocker with a potential inhibitor of fusion may yield greater efficacy. To this end we also tested combination of CA45 with FVM04. Combination of FVM04 and CA45 at 5 mg/kg each (FIG. 5B upper panel) or 5 mg/kg of FVM04 plus 2.5 mg/kg of CA45 (FIG. 5B, lower panel) provided 100% protection against SUDV in two independent experiments. Although comparison of survival curves between the groups treated with cocktail versus individual antibodies did not show statistical significance, it was remarkable that, in contrast to monotherapy, mice treated with a cocktail of CA45 and FVM04 showed no weigh loss (FIG. 5B) or other signs of disease (data not shown).

We then tested CA45 and FVM04 alone and in combination in a stringent model of EBOV infection in guinea pigs in which a single dose of antibody is delivered at 3 dpi. Groups of 6 guinea pigs were infected with 1000 LD$_{50}$ of guinea pig-adapted EBOV (GPA-EBOV) and treated at 3 dpi with either FVM04 or CA45 at 5 mg/animal or combination of the two mAbs at 2.5 or 5 mg each. A group of 4 animals was treated with PBS as negative control. Treatment with 5 mg of FVM04 or CA45 alone protected only 1 out of 6 and 3 out of 6 animals respectively (FIG. 5C). All PBS treated animals died within 8 dpi (median survival: 7.5) and lost an average of 21% of body weight before succumbing to infection, while FVM04 or CA45 treated animals showed a median survival of 11.5 and 20.5 days and maximum weight loss of 9.2% and 1.2% respectively (FIG. 5C). In contrast all animals treated with a combination of either 2.5 or 5 mg of each mAb survived the infection with no sign of disease or weight loss (FIG. 5C). The protection afforded by either monotherapy or combination was statistically significant (p=0.0018 and P<0.0001 respectively) in comparison to PBS group. Similarly, comparison of each monotherapy group with the combined cocktail groups showed highly significant difference (CA45 vs. cocktails 0.0079, FVM04 vs. cocktails <0.0001). These data combined with the lack of weight loss in cocktail treated groups indicates strong synergy between the two antibodies.

We had previously shown that FVM04 alone (5 mg) protects against SUDV infection in guinea pigs. Here we evaluated if CA45 can also protect against SUDV in this model. As shown in FIG. 5D, a single dose of 5 mg CA45 at 3 dpi protected all animals from lethal infection with GPA-SUDV while all control guinea pigs died within 14 dpi (p<0.0001).

Example 6: Efficacy in Ferret Model of BDBV Infection

Efficacy of the combination of FVM04 and CA45 was tested in a ferret model of BDBV infection (Kozak, et al., 2016, *J Virol*, JVI.01033-16). Six ferrets were infected with BDBV and on day 3 and 6 post infection 4 ferrets received an intraperitoneal injection of 20 mg of each CA45 and FVM04, while the other two ferrets received PBS. Animals were monitored for 28 days post-challenge. A shown in FIG. 6, all four animals treated with the antibody cocktail survived the challenge, while the two control animals succumbed to infection.

These data further indicate that a combination of antibodies targeting the receptor binding site (like FVM04) an antibody targeting the internal fusion loop (like CA45) is capable of controlling the infection with multiple ebolaviruses.

The breadth and scope of the present disclosure should not be limited by any of the above-described exemplary embodiments, but should be defined only in accordance with the following claims and their equivalents.

SEQUENCE TABLE

| SEQ ID NO | Description | Sequence |
|---|---|---|
| 1 | CA45 VH | QVQLQEWGEGLVKPSETLSLTCAVYGGSISGYYHW NWIRLPPGKGLEWIGNIDNSASTNYNPSLKTRVTI SKDTSKNQISLKVRSLTAADTAVYYCARDPGFTIF GVVITSWSGLDSWGQGAVVTVSS |
| 2 | CA45 VL entire | DIQMTQSPSSLSASVGDTVTITCRASQSISNNLAW YQQRPRRAPQLLIYAASNLASGVPSRFSGSGSGTD FTLTISSLQAEDFAAYYCQQHNTLPLTFGGGTKVE |
| 3 | CA45 CDRH1 | IGYYHWN |
| 4 | CA45 CDRH2 | GNIDNSASTNYNPSLKT |
| 5 | CA45 CDRH3 | DPGFTIFGVVITSWSGLDS |
| 6 | CA45 CDRL1 | RASQSISNNLA |
| 7 | CA45 CDRL2 | AASNLA |
| 8 | CA45 CDRL3 | QQHNTLPLT |
| 9 | CA45 CDRH1 generic | G-Y-Y-X1-W-X2, where X1 and X2 are any amino acid |
| 10 | CA45 CDRH3 Generic | D-X1-G-X2-T-I-F-X3-X4-X5-I-X6-X7-W-X8-X9-X10-D-X12, where X1 to X12 are any amino acid |
| 11 | EBOV Makona gp | >gi\|1050758570\|emb\|SCD11534.1\| virion spike glycoprotein precursor [Ebola virus] MGVTGILQLPRDRFKRTSFFLWVIILFQRTFSIPL |

| SEQ ID NO | Description | Sequence |
|---|---|---|
| | | GVIHNSTLQVSDVDKLVCRDKLSSTNQLRSVGLNL EGNGVATDVPSVTKRWGFRSGVPPKVVNYEAGEWA ENCYNLEIKKPDGSECLPAAPDGIRGFPRCRYVHK VSGTGPCAGDFAFHKEGAFFLYDRLASTVIYRGTT FAEGVVAFLILPQAKKDFSSHPLREPVNATEDPS SGYYSTTIRYQATGFGTNETEYLFEVDNLTYVQLE SRFTPQFLLQLNETIYASGKRSNTTGKLIWKVNPE IDTTIGEWAFWETKKNLTRKIRSEELSFTAVSNGP KNISGQSPARTSSDPETNTTEDHKIMASENSSAM VQVHSQGRKAAVSHLTTLATISTSPQPPTTKTGPD NSTHNTPVYKLDISEATQVGQHHRRADNDSTASDT PPATTAAGPLKAENTNTSKSADSLDLATTTSPQNY SETAGNNNTHHQDTGEESASSGKLGLITNTIAGVA GLITGGRRTRREVIVNAQPKCNPNLHYWTTQDEGA AIGLAWIPYFGPAAEGIYTEGLMHNQDGLICGLRQ LANETTQALQLFLRATTELRTFSILNRKAIDFLLQ RWGGTCHILGPDCCIEPHDWTKNITDRIDQIIHDF VDKTLPDQGDNDNWWTGWRQWIPAGIGVTGVIIAV IALFCICKFVF |
| 12 | EBOV Mayinga gp | >gi\|4262350\|gb\|AAD14585.1\| virion spike glycoprotein precursor [Ebola virus-Mayinga, Zaire, 1976] MGVTGILQLPRDRFKRTSFFLWVIILFQRTFSIPL GVIHNSTLQVSDVDKLVCRDKLSSTNQLRSVGLNL EGNGVATDVPSATKRWGFRSGVPPKVVNYEAGEWA ENCYNLEIKKPDGSECLPAAPDGIRGFPRCRYVHK VSGTGPCAGDFAFHKEGAFFLYDRLASTVIYRGTT FAEGVVAFLILPQAKKDFSSHPLREPVNATEDPS SGYYSTTIRYQATGFGTNETEYLFEVDNLTYVQLE SRFTPQFLLQLNETIYTSGKRSNTTGKLIWKVNPE IDTTIGEWAFWETKKNLTRKIRSEELSFTVVSNGA KNISGQSPARTSSDPGTNTTTEDHKIMASENSSAM VQVHSQGREAAVSHLTTLATISTSPQSLTTKPGPD NSTHNTPVYKLDISEATQVEQHHRRTDNDSTASDT PSATTAAGPPKAENTNTSKSTFDLDPATTTSPQNH SETAGNNNTHHQDTGEESASSGKLGLITNTIAGVA GLITGGRRTRREAIVNAQPKCNPNLHYWTTQDEGA AIGLAWIPYFGPAAEGIYIEGLMHNQDGLICGLRQ LANETTQALQLFLRATTELRTFSILNRKAIDFLLQ RWGGTCHILGPDCCIEPHDWTKNITDKIDQIIHDF VDKTLPDQGDNDNWWTGWRQWIPAGIGVTGVIIAV IALFCICKFVF |
| 13 | EBOV Kikwit gp | >gi\|965570359\|gb\|ALT19754.1\| envelope glycoprotein [Ebola virus] MGVTGILQLPRDRFKRTSFFLWVIILFQRTFSIPL GVIHNSTLQVSDVDKLVCRDKLSSTNQLRSVGLNL EGNGVATDVPSATKRWGFRSGVPPKVVNYEAGEWA ENCYNLEIKKPDGSECLPAAPDGIRGFPRCRYVHK VSGTGPCAGDFAFHKEGAFFLYDRLASTVIYRGTT FAEGVVAFLILPQAKKDFSSHPLREPVNATEDPS SGYYSTTIRYQATGFGTNETEYLFEVDNLTYVQLE SRFTPQFLLQLNETIYTSGKRSNTTGKLIWKVNPE IDTTIGEWAFWETKKNLTRKIRSEELSFTAVSNRA KNISGQSPARTSSDPGTNTTTEDHKIMASENSSAM VQVHSQGREAAVSHLTTLATISTSPQPPTTKPGPD NSTHNTPVYKLDISEATQVEQHHRRTDNDSTASDT PPATTAAGPLKAENTNTSKGTDLLDPATTTSPQNH SETAGNNNTHHQDTGEESASSGKLGLITNTIAGVA GLITGGRRARREAIVNAQPKCNPNLHYWTTQDEGA AIGLAWIPYFGPAAEGIYIEGLMHNQDGLICGLRQ LANETTQALQLFLRATTELRTFSILNRKAIDFLLQ RWGGTCHILGPDCCIEPHDWTKNITDKIDQIIHDF VDKTLPDQGDNDNWWTGWRQWIPAGIGVTGVIIAV IALFCICKFVF |
| 14 | SUDV gulu gp | >gi\|32815056\|gb\|AAP88031.1\| structural glycoprotein [Sudan ebolavirus] MGGLSLLQLPRDKFRKSSFFVWVIILFQKAFSMPL GVVTNSTLEVTEIDQLVCKDHLASTDQLKSVGLNL EGSGVSTDIPSATKRWGFRSGVPPKVVSYEAGEWA ENCYNLEIKKPDGSECLPPPPDGVRGFPRCRYVHK AQGTGPCPGDYAFHKDGAFFLYDRLASTVIYRGVN FAEGVIAFLILAKPKETFLQSPPIREAVNYTENTS SYYATSYLEYEIENFGAQHSTTLFKIDNNTFVRLD RPHTPQFLFQLNDTIHLHQQLSNTTGRLIWTLDAN INADIGEWAFWENKKNLSEQLRGEELSFEALSLNE TEDDDAASSRITKGRISDRATRKYSDLVPKNSPGM VPLHIPEGETTLPSQNSTEGRRVGVNTQETITETA ATIIGTNGNHMQISTIGIRPSSSQIPSSSPTTAPS PEAQTPTTHTSGPSVMATEEPTTPPGSSPGPTTEA PTLTTPENITTAVKTVLPQESTSNGLITSTVTGIL GSLGLRKRSRRQTNTKATGKCNPNLHYWTAQEQHN AAGIAWIPYFGPGAEGIYTEGLMHNQNALVCGLRQ LANETTQALQLFLRATTELRTYTILNRKAIDFLLR RWGGTCRILGPDCCIEPHDWTKNITDKINQIIHDF IDNPLPNQDNDDNWWTGWRQWIPAGIGITGIIIAI IALLCVCKLLC |
| 15 | BDBV gp | >gi\|499104260\|gb\|AGL73474.1\| glycoprotein [Bundibugyo ebolavirus] MVTSGILQLPRERFRKTSFFVWVIILFHKVFPIPL GVVHNNTLQVSDIDKLVCRDKLSSTQLKSVGLNL EGNGVATDVPTATKRWGFRAGVPPKVVNYEAGEWA ENCYNLDIKKADGSECLPEAPEGVRGFPRCRYVHK VSGTGPCPEGFAFHKEGAFFLYDRLASTIIYRSTT FSEGVVAFLILPKTKKDFFQSPPLHEPANMTTDPS SYYHTVTLNYVADNFGTNMTNFLFQVDHLTYVQLE PRFTPQFLVQLNETIYTNGRRSNTTGTLIWKVNPT VDTGVGEWAFWENKKNFTKTLSSEELSVILVPRAQ DPGSNQKTKVTPTSFANNQTSKNHEDLVPKDPASV VQVRDLQRENTVPTSPLNTVPTTLIPDTMEEQTTS HYELPNISGNHQERNNTAHPETLANNPPDNTTPST PPQDGERTSSHTTPSPRPVPTSTIHPTTRETQIPT TMITSHDTDSNRPNPIDISESETEPGLLTNTIRGV ANLLTGSRRTRREITLRTQAKCNPNLHYWTTQDEGA AIGLAWIPYFGPAAEGIYTEGIMHNQNGLICGLRQ LANETTQALQLFLRATTELRTFSILNRKAIDFLLQ RWGGTCHILGPDCCIEPHDWTKNITDKIDQIIHDF IDKPLPDQTDNDNWWTGWRQWVPAGIGITGVIIAV IALLCICKFLL |
| 16 | TAFV gp | >gi\|302315373\|ref\|YP_003815426.1\| spike glycoprotein [Tai Forest ebolavirus] MGASGILQLPRERFRKTSFFVWVIILFHKVFSIPL GVVHNNTLQVSDIDKFVCRDKLSSTQLKSVGLNL EGNGVATDVPTATKRWGFRAGVPPKVVNCEAGEWA ENCYNLAIKKSDGSECLPEAPEGVRGFPRCRYVHK VSGTGPCPGGLAFHKEGAFFLYDRLASTIIYRGTT FAEGVIAFLILPKARKDFFQSPPLHEPANMTTDPS SYYHTTTINYVVDNFGTNTTEFLFQVDHLTYVQLE ARFTPQFLVLLNETIYSDNRRSNTTGKLIWKINPT VDTSMGEWAFWENKKNFTKTLSSEELSFVPVPETQ NQVLDTTATVSPPISAHNHAAEDHKELVSEDSTPV VQMQNIKGKDTMPTTVTGVPTTTPSPFPINARNTD HTKSFIGLEGPQDEHSTTQPAKTTSQPTNSTESTT LNPTSEPSSRGTGPSSPTVPNTTESHAELGKTTPT TLPEQHTAASAIPRAVHPDELSGPGFLTNTIRGVT NLLTGSRRKRRDVTPNTQPKCNPNLHYWTALDEGA AIGLAWIPYFGPAAEGIYTEGIMENQNGLICGLRQ LANETTQALQLFLRATTELRTFSILNRKAIDFLLQ RWGGTCHILGPDCCIEPQDWTKNITDKIDQIIHDF VDNNLPNQNDGSNWWTGWKQWVPAGIGITGIIIAI IALLCICKFML |
| 17 | RESTV gp | >gi\|440385035\|gb\|AGC02898.1\| structural glycoprotein [Reston ebolavirus] MGSGYQLLQLPRERFRKTSFLVWAIILFQRAISMP LGIVTNSTLKATEIDQLVCRDKLSSTQLKSVGLN LEGNGIATDVPSATKRWGFRSGVPPKVVSYEAGEW AENCYNLEIKKSDGSECLPPPPDGVRGFPRCRYVH |

SEQUENCE TABLE

| SEQ ID NO | Description | Sequence |
|---|---|---|
| | | KVQGTGPCPGDLAFHKNGAFFLYDRLASTVIYRGT TFAEGVIAFLILSEPRKHFWKATPAHEPVNTTDDS TSYYITLTLSYEMSNFGGEESNTLFKVDNHTYVQL DRPHTPQFVLQLNETLRRNNRLSNSTGRLTWTLDP KIEPNVGEWAFWETKKNFSKQLQGENLHFQILSTH TNNSSDQSPAGTVQGKISYHPPTNNSELVPTDSPP VVSVLTAGRTEEMSTQGLTNGETITGFTANPMTTT IALSPTMTSKVDNNVPSEQPNNTTSIEDSPPSASN ETIDHSEMNSIQGSNNSTQSPQTKTKPAPTASLMT LGPQETANSSKPGTSPGSAAEPSQPGLTINTVSKV ADSLSPTRKQKRSVRQNTANECNPDLHYWTAVDEG AAVGLAWIPYFGPAAEGIYIEGVMHNQNGLICGLR QLANETTQALQLFLRATTELRTYSLLNRKAIDFLL QRWGGTCRILGPSCCIEPHDWTKNITDEINQIKHD FIDNPLPDHGDDLNLWTGWRQWIPAGIGIIGVIIA ITALLCICKILC |
| 18 | MARV Ravn gp | >gi\|2459878\|gb\|AAC40459.1\| glycoprotein precursor [Marburg marburgvirus] MKTIYFLISLILIQSIKTLPVLEIASNSQPQDVDS VCSGTLQKTEDVHLMGFTLSGQKVADSPLEASKRW AFRTGVPPKNVEYTEGEEEAKTCYNISVTDPSGKSL LLDPPSNIRDYPKCKTVHHIQGQNPHAQGIALHLW GAFFLYDRVASTTMYRGKVFTEGNIAAMIVNKTVH RMIFSRQGQGYRHMNLTSTNKYWTSSNETQRNDTG CFGILQEYNSTNNQTCPPSLKPPSLPTVTPSIHST NTQINTAKSGTMNPSSDDEDLMISGSGSGEQGPHT TLNVVTEQKQSSTILSTPSLHPSTSQHEQNSTNPS RHAVTEHNGTDPTTQPATLLNNTNTTPTYNTLKYN LSTPSPPTRNITNNDTQRELAESEQTNAQLNTTLD PTENPTTGQDTNSTTNIIMTTSDITSKHPTNSSPD SSPTTRPPIYFRKKRSIFWKEGDIFPFLDGLINTE IDFDPIPNTETIFDESPSFNTSTNEEQHTPPNISL TFSYFPDKNGDTAYSGENENDCDAELRIWSVQEDD LAAGLSWIPFFGPGIEGLYTAGLIKNQNNLVCRLR RLANQTAKSLELLLRVTTEERTFSLINRHAIDFLL TRWGGTCKVLGPDCCIGIEDLSKNISEQIDKIRKD EQKEETGWLGGKWWTSDWGVLTNLGILLLLSIAV LIALSCICRIFTKYIG |
| 19 | MARV angola gp | >gi\|674654027\|gb\|AIL25245.1\| glycoprotein [Marburg marburgvirus] MKTTCLLISLILIQGVKTLPILEIASNIQPQNVDS VCSGTLQKTEDVHLMGFTLSGQKVADSPLEASKRW AFRAGVPPKNVEYTEGEEEAKTCYNISVTDPSGKSL LLDPPTNIRDYPKCKTIHHIQGQNPHAQGIALHLW GAFFLYDRIASTTMYRGKVFTEGNIAAMIVNKTVH KMIFSRQGQGYRHMNLTSTNKYWTSSNGTQTNDTG CFGTLQEYNSTKNQTCAPSKKPLPLPTAHPEVKLT STSTDATKLNTTDPNSDDEDLTTSGSGSGEQEPYT TSDAATKQGLSSTMPPTPSPQPSTPQQGGNNTNHS QGVVTEPGKTNTTAQPSMPPHNTTTISTNNTSKHN LSTPSVPIQNATNYNTQSTAPENEQTSAPSKTTLL PTENPTTAKSTNSTKSPTTTVPNTTNKYSTSPSPT PDSTAQHLVYFRRKRNILWREGDMFPFLDGLINAP IDFDPVPNTKTIFDESSSSGASAEEDQHASPNISL TLSYFPKVNENTAHSGENENDCDAELRIWSVQEDD LAAGLSWIPFFGPGIEGLYTAGLIKNQNNLVCRLR RLANQTAKSLELLLRVTTEERTFSLINRHAIDFLL ARWGGTCKVLGPDCCIGIEDLSRNISEQIDQIKKD EQKEGTGWGLGGKWWTSDWGVLTNLGILLLLSIAV LIALSCICRIFTKYIG |
| 20 | FVM04 VH | EVQLVQSGGGLVQPGGSMRLSCEASGLSLSDYFMH WVRQAQGKGLEWIGLIQTKAFTYKTEYPAAVKGRF TISRDDSKNTLYLQMSSLKPEDTALYYCIAVTPDF YYWGQGVLVTVSS |
| 21 | FVM04 VL | DVVMTQSPSFLSASVGDRVTITCRASQDITINLNW FQHKPGKAPKRLIYVASRLERGVPSRFSGSGSGTE FTLTISSLQPEDFATYYCQQYNNYPLTFGPGTKLD IKRTV |
| 22 | FVM04 CDRH1 | GLSLSDYFMH |
| 23 | FVM04 CDRH2 | IQTKAFTYKT |
| 24 | FVM04 CDRH3 | IAVTPDFYY |
| 25 | FVM04 CDRL1 | QDITIN |
| 26 | FVM04 CDRL2 | VAS |
| 27 | FVM04 CDRL3 | QQYNNYPLT |

What is claimed is:

1. An isolated antibody or antigen-binding fragment thereof comprising a binding domain that specifically binds to an epitope in the internal fusion loop of a Filovirus glycoprotein, wherein the binding domain comprises a heavy chain variable region (VH) and a light chain variable region (VL);
   (a) wherein the VH comprises heavy chain complementarity determining regions CDRH1, CDRH2, and CDRH3; wherein CDRH1 comprises SEQ ID NO: 3; wherein CDRH2 comprises SEQ ID NO: 4, and wherein CDRH3 comprises SEQ ID NO: 5; and
   (b) wherein the VL comprises light chain complementarity determining regions CDRL1, CDRL2, and CDRL3; wherein CDRL1 comprises SEQ ID NO: 6; wherein CDRL2 comprises SEQ ID NO: 7; and wherein CDRL3 comprises SEQ ID NO: 8.

2. The antibody or fragment thereof of claim 1, wherein the VH comprises an amino acid sequence at least 80%, 85%, 90%, 95%, or 100% identical to SEQ ID NO: 1, and wherein the VL comprises an amino acid sequence at least 80%, 85%, 90%, 95%, or 100% identical to SEQ ID NO: 2.

3. The antibody or fragment thereof of claim 1, wherein the VH comprises the amino acid sequence SEQ ID NO: 1 and wherein the VL comprises the amino acid sequence SEQ ID NO: 2.

4. The antibody or fragment thereof of claim 1, which is a non-human primate antibody, a human antibody, a murine antibody, a humanized antibody, a chimeric antibody, or a fragment thereof.

5. The antibody or fragment thereof of claim 1, which is a monoclonal antibody, a component of a polyclonal antibody mixture, a recombinant antibody, a multispecific antibody, or any combination thereof.

6. The antibody or fragment thereof of claim 1, which is a bispecific antibody or fragment thereof further comprising a heterologous binding domain.

7. The antibody or fragment thereof of claim 6, wherein the heterologous binding domain can specifically bind to a filovirus GP1/GP2 base epitope, a filovirus GP receptor binding site (RBS) epitope, a filovirus GP glycan cap epitope, a filovirus GP internal fusion loop (IFL) epitope, or any combination thereof.

8. The antibody or fragment thereof of claim 1, comprising an Fv fragment, an Fab fragment, an F(ab')2 fragment, an Fab' fragment, a dsFv fragment, an scFv fragment, an scFab fragment, an sc(Fv)2 fragment, or any combination thereof.

9. The antibody or fragment thereof of claim 1, which can neutralize the infectivity of EBOV, SUDV, BDBV, RESTV, or any combination thereof.

10. The antibody or fragment thereof of claim 1, which is conjugated to an antiviral agent, a protein, a lipid, a detectable label, a polymer, or any combination thereof.

11. A composition comprising the antibody or fragment thereof of claim 1, and a carrier.

12. A method for treating Filovirus infection in a subject, comprising administering to a subject in need thereof an effective amount of the antibody or antigen binding fragment thereof of claim 1.

* * * * *

UNITED STATES PATENT AND TRADEMARK OFFICE
CERTIFICATE OF CORRECTION

PATENT NO. : 11,186,626 B2  
APPLICATION NO. : 16/340996  
DATED : November 30, 2021  
INVENTOR(S) : Aman et al.

Page 1 of 1

It is certified that error appears in the above-identified patent and that said Letters Patent is hereby corrected as shown below:

In the Specification

Column 1, Lines 20-25 presently read "This invention was made with government support under Grant No. A1098178 awarded by the National Institutes of Health. This invention was made with government support under Contract No. HDTRA-13-C-0015 awarded by the Defense Threat Reduction Agency (DTRA). The government has certain rights in the invention."

Should instead read "This invention was made with government support under HDTRA1-13-C-0015 awarded by the Defense Threat Reduction Agency, and AI098178 awarded by the National Institutes of Health. The government has certain rights in the invention."

Signed and Sealed this  
Thirtieth Day of July, 2024

Katherine Kelly Vidal  
*Director of the United States Patent and Trademark Office*